US011123008B2

(12) United States Patent
Cunningham et al.

(10) Patent No.: US 11,123,008 B2
(45) Date of Patent: Sep. 21, 2021

(54) FEEDING TRANSITION NIPPLE MECHANISM AND SYSTEM

(71) Applicant: NFANT Labs, LLC, Atlanta, GA (US)

(72) Inventors: Thomas J. Cunningham, Smyrna, GA (US); Louis F. Malice, Jr., Marietta, GA (US); Moreed Khosravanipour, Atlanta, GA (US); Gilson J. Capilouto, Lexington, KY (US)

(73) Assignee: NFANT Labs LLC, Atlanta, GA (US)

( * ) Notice: Subject to any disclaimer, the term of this patent is extended or adjusted under 35 U.S.C. 154(b) by 499 days.

(21) Appl. No.: 15/945,864

(22) Filed: Apr. 5, 2018

(65) Prior Publication Data

US 2018/0220955 A1 Aug. 9, 2018

Related U.S. Application Data

(60) Continuation-in-part of application No. 15/601,066, filed on May 22, 2017, now Pat. No. 10,085,686, which is a division of application No. 14/665,644, filed on Mar. 23, 2015, now Pat. No. 9,687,192, which is a continuation-in-part of application No. 14/166,281, filed on Jan. 28, 2014, now Pat. No. 8,986,229, which is a division of application No. 13/479,640, filed on May 24, 2012, now Pat. No. 8,663,131.

(Continued)

(51) Int. Cl.
| | |
|---|---|
| *A61B 5/00* | (2006.01) |
| *A61B 5/03* | (2006.01) |
| *A61J 11/00* | (2006.01) |
| *A61B 5/11* | (2006.01) |
| *A61B 5/22* | (2006.01) |
| *A61J 9/00* | (2006.01) |

(52) U.S. Cl.
CPC ........... *A61B 5/4552* (2013.01); *A61B 5/038* (2013.01); *A61B 5/1114* (2013.01); *A61B 5/682* (2013.01); *A61J 11/00* (2013.01); *A61B 5/002* (2013.01); *A61B 5/228* (2013.01); *A61B 2503/04* (2013.01); *A61B 2560/0462* (2013.01); *A61B 2562/0247* (2013.01);
(Continued)

(58) Field of Classification Search
CPC ..... A61B 5/4552; A61B 5/038; A61B 5/1114; A61B 5/682; A61J 11/00
USPC ........................................................ 600/590
See application file for complete search history.

(56) References Cited

U.S. PATENT DOCUMENTS

| | | |
|---|---|---|
| 5,544,766 A | 3/1996 | Dunn et al. |
| 5,897,007 A | 4/1999 | Schein et al. |

(Continued)

FOREIGN PATENT DOCUMENTS

JP 2007075212 A 3/2007

*Primary Examiner* — Daniel L Cerioni
(74) *Attorney, Agent, or Firm* — Quinn IP Law

(57) ABSTRACT

A feeding transition system for transitioning an infant subject to oral feeding includes at least one no-flow nipple and at least one flow nipple. The no-flow nipple has a fully enclosed tip portion such that no fluid can flow directly from the nipple cavity through the nipple wall. The flow nipple is formed of a no-flow nipple having an aperture formed in the tip portion for flowing fluid from the nipple cavity through the nipple wall. The system includes a bolus delivery nipple formed of a no-flow nipple including a bolus delivery conduit disposed in the nipple cavity and in fluid communication with a reservoir of fluid. The bolus delivery conduit includes a conduit outlet attached to the nipple wall to output a bolus of fluid from the tip portion of the bolus delivery nipple via the outlet. A method for transitioning an infant subject to oral feeding is provided.

32 Claims, 7 Drawing Sheets

Related U.S. Application Data

(60) Provisional application No. 62/482,994, filed on Apr. 7, 2017, provisional application No. 61/578,004, filed on Dec. 20, 2011, provisional application No. 61/490,892, filed on May 27, 2011.

(52) U.S. Cl.
CPC . *A61B 2562/0261* (2013.01); *A61B 2562/168* (2013.01); *A61J 9/00* (2013.01); *A61J 11/001* (2013.01)

(56) References Cited

U.S. PATENT DOCUMENTS

| | | |
|---|---|---|
| 6,126,679 A | 10/2000 | Botts |
| 6,129,703 A | 10/2000 | Beneke |
| 6,200,295 B1 | 3/2001 | Burchett et al. |
| 8,663,131 B2 | 3/2014 | Cunningham et al. |
| 9,561,002 B2 | 2/2017 | Lau |
| 2004/0164043 A1 | 8/2004 | Hakim |
| 2004/0188372 A1 | 9/2004 | Ruth et al. |
| 2006/0129127 A1* | 6/2006 | Ruth .................. A61J 9/00 604/514 |
| 2008/0039778 A1 | 2/2008 | Goldie et al. |
| 2009/0156967 A1 | 6/2009 | Cohen |
| 2012/0302924 A1* | 11/2012 | Cunningham ......... A61B 5/228 600/590 |
| 2013/0056435 A1* | 3/2013 | Itzek .................. A61J 9/00 215/11.5 |
| 2013/0186915 A1 | 7/2013 | Al Thalab |
| 2015/0208979 A1 | 7/2015 | Cunningham et al. |
| 2015/0231038 A1* | 8/2015 | Oates, II ............... A61J 7/0053 604/79 |
| 2016/0310367 A1 | 10/2016 | Lin |

* cited by examiner

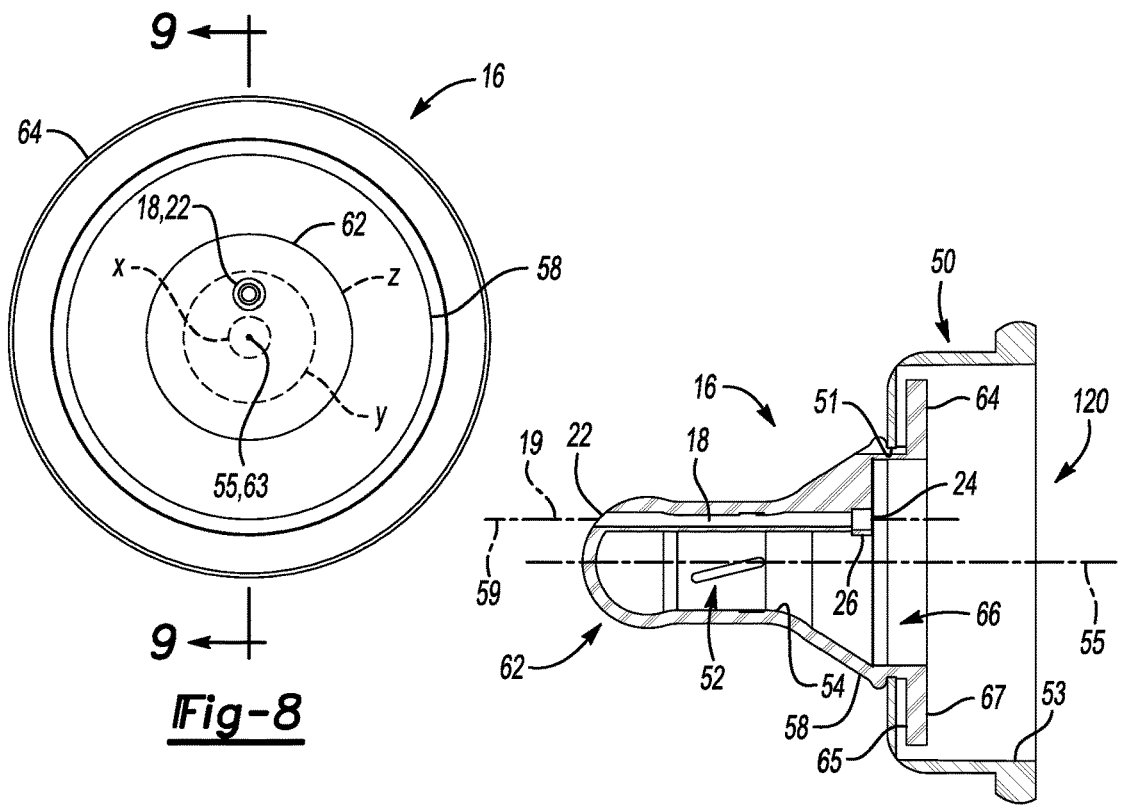
Fig-8
Fig-9
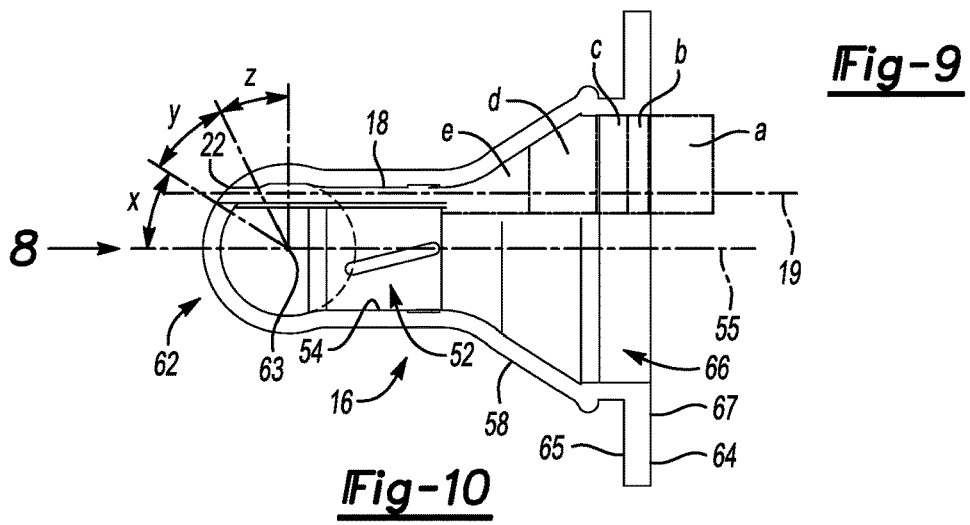
Fig-10
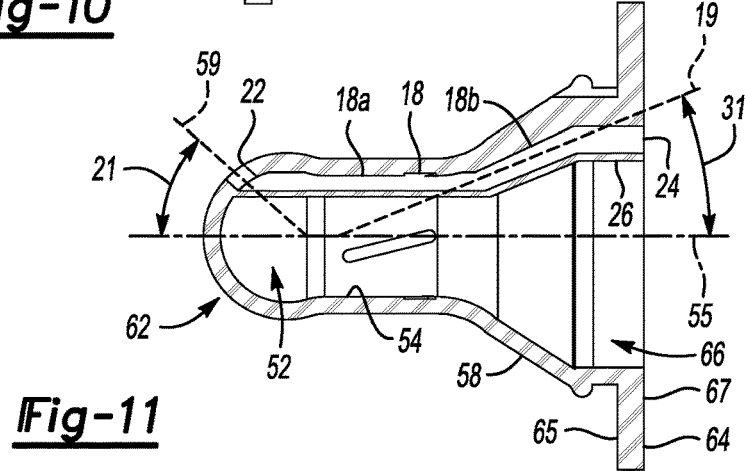
Fig-11

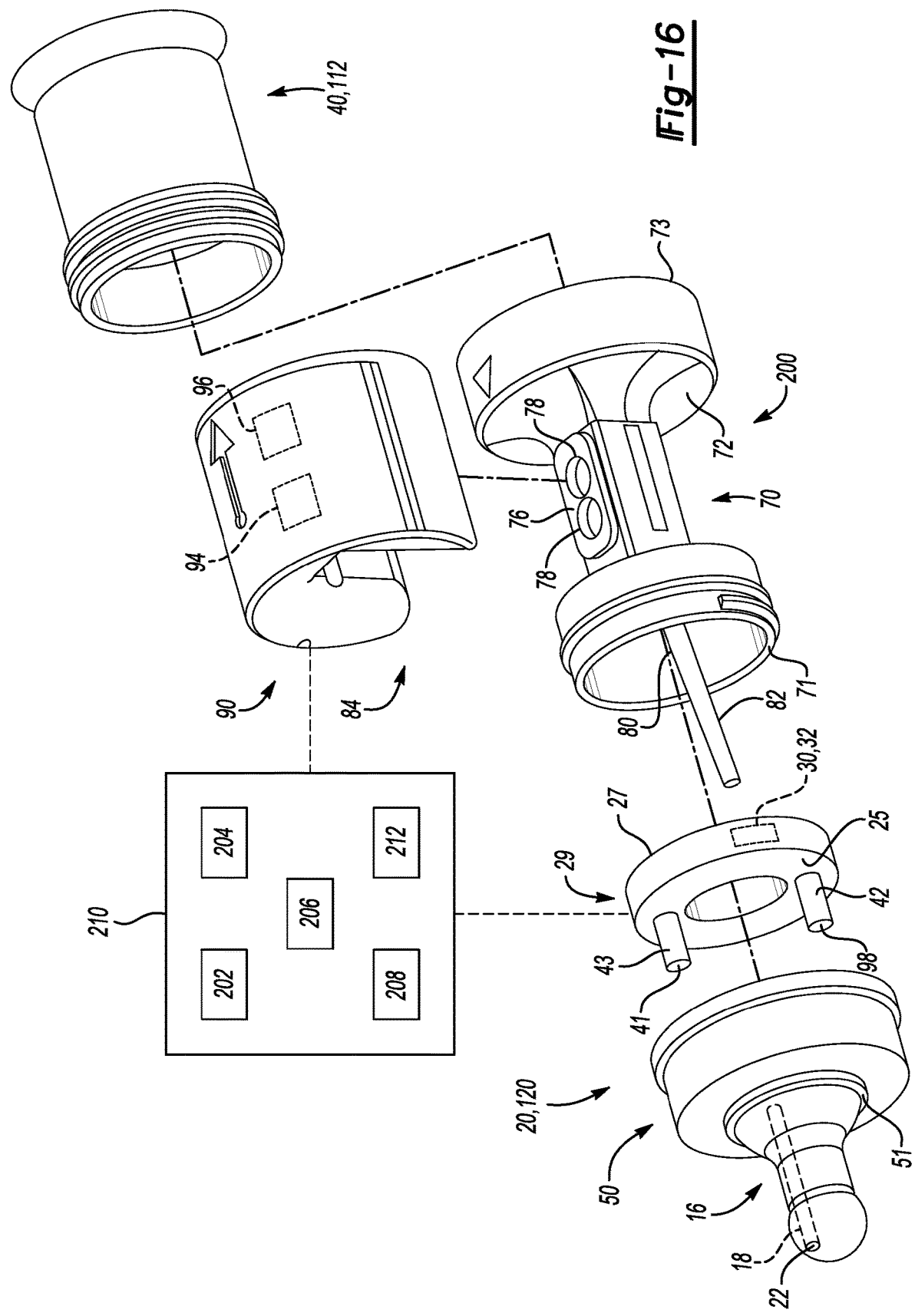

FEEDING TRANSITION NIPPLE MECHANISM AND SYSTEM

CROSS-REFERENCE TO RELATED APPLICATIONS

This Application claims the benefit of U.S. provisional application 62/482,994 filed Apr. 7, 2017, U.S. non-provisional application Ser. No. 15/601,066 filed May 22, 2017, U.S. non-provisional application Ser. No. 14/665,644 filed Mar. 23, 2015 and issued as U.S. Pat. No. 9,687,192 on Jun. 27, 2017, U.S. non-provisional application Ser. No. 14/166,281 filed Jan. 28, 2014 and issued as U.S. Pat. No. 8,986,229 on Mar. 24, 2015, U.S. non-provisional application Ser. No. 13/479,640 filed May 24, 2012 and issued as U.S. Pat. No. 8,663,131 on Mar. 4, 2014, U.S. provisional application 61/490,892 filed May 27, 2011, and U.S. provisional application 61/578,004 filed Dec. 20, 2011, which are each hereby incorporated by reference in their entirety. U.S. non-provisional application Ser. No. 15/601,066 is a continuation of U.S. non-provisional application Ser. No. 14/665,644 which is a continuation-in-part of U.S. non-provisional application Ser. No. 14/166,281 which is a divisional application of U.S. non-provisional application Ser. No. 13/479,640 which is a non-provisional application of U.S. provisional application 61/490,892 and U.S. provisional application 61/578,004.

TECHNICAL FIELD

The present disclosure pertains to feeding transition system, and in particular, a feeding transition system including a nipple mechanism for bolus delivery.

BACKGROUND

Late and moderate preterm births (LMPT) constitute 84% of all preterm births and feeding difficulties, including difficulty of the infant to transition to oral feeding on their own, occur in 30-40%. Feeding problems among late preterm infants (34-37 weeks gestation) approaches five times that of term infants (34% vs. 7%). For moderate preterm infants (32-33 weeks gestation) the National Institute of Child Health and Human Development (NICHD) Neonatal Research network reported that 85% of moderate preterm infants remained in the hospital at 36 weeks due to apnea, feeding difficulties, or inadequate weight gain. Feeding difficulty for these babies leads to poor weight gain and growth, as well as an increased risk for associated morbidities including dehydration Immature and ineffective suck-swallow coordination and difficulty of the infant to transition to oral feeding on their own are reported as primary reasons for the high incidence of reported feeding issues among LMPT while in the NICU. Variability in feeding practice is cited as a likely reason for the high rate of rehospitalization in this population. Variability in feeding practice includes bolus trial protocols which do not simulate bottle feeding, for example, by using pacifiers or catheters routed externally to a nipple into the baby's oral cavity, neither of which simulates bottle feeding. For example, contact with the catheter during fluid (bolus) delivery by the infant's tongue is inconsistent with contact made with a feeding nipple, and interferes with the infant's ability to adapt to bottle feeding, e.g., interferes with infant's ability to develop suck-swallow coordination using a nipple.

SUMMARY

Providing consistent environmental factors and feeding constructs to an infant can help with the ease of transition of the infant to self-sustained oral feeding. Provided herein are a feeding transition nipple mechanism and system, and a method of use, for transitioning an infant to oral feeding. The system includes a set of nipples which can include a no-flow nipple, a series of flow nipples each having a different flow rate, and a bolus delivery nipple for actuated delivery of a bolus to an infant during feeding. The series of flow nipples can include an extra slow flow (ESF) nipple, a slow flow (SLF) nipple, and a standard flow (STF) nipple, for use in transitioning an infant to oral feeding. In one example, all the nipples in the nipple set have a similar shape, size, texture and material, to provide a consistent feeding environment to an infant being transitioned to oral feeding using the nipple set with the method described herein. The consistent shape, texture, etc. of the plurality of nipples in the nipple set, and the use of a nipple for bolus delivery, provides consistent feeding environmental factors and consistent feeding constructs which aid in easing transition of and infant to oral feeding. The bolus delivery mechanism provided herein includes a delivery conduit integrated with a nipple, such that the delivery conduit is contained with the nipple so as not to interfere with the infant's development of suck-swallow coordination with the nipple. The delivery conduit is fluidly connected to a reservoir containing the bolus fluid, and delivery is actuated by an actuator, which may be manually or automatically controlled and/or actuated.

In one example, the feeding transition nipple system provided herein can be used in conjunction with the feeding performance evaluation system having common inventorship with the present disclosure, disclosed in U.S. non-provisional application Ser. No. 15/601,066 filed May 22, 2017, U.S. non-provisional application Ser. No. 14/665,644 filed Mar. 23, 2015 and issued as U.S. Pat. No. 9,687,192 on Jun. 27, 2017, U.S. non-provisional application Ser. No. 14/166,281 filed Jan. 28, 2014 and issued as U.S. Pat. No. 8,986,226 on Mar. 24, 3015, and U.S. non-provisional application Ser. No. 13/479,640 filed May 24, 2012 and issued as U.S. Pat. No. 8,663,131 on Mar. 4, 2014, the entire disclosure of each being incorporated by reference herein. In one example, the method for transitioning an infant to oral feeding includes using feeding performance information gathered from the feeding performance evaluation system to select a nipple or sequence of nipples from the feeding transition nipple set, and to evaluate the infant's response to the selected nipple or sequence of nipples. In another example, the bolus delivery mechanism can be integrated with the feeding performance evaluation system such that bolus delivery can be actuated in response to the infant's suck-swallow performance as measured and/or evaluated using the feeding performance evaluation system.

In an illustrative example, a feeding transition system for transitioning an infant subject to oral feeding is provided. The system comprises a no-flow nipple, a plurality of flow nipples, and a bolus delivery nipple. In one example, each of the flow nipples and the bolus delivery nipple is a modification of the no-flow nipple such that each of the no-flow, flow and bolus delivery nipples have the same exterior shape and size, have the same texture and are made of the same material, to provide a consistent feeding environment to an infant being transitioned to oral feeding using a combination of the no-flow nipple, the flow nipples and/or the bolus delivery nipple with the method of transitioning the infant subject to oral feeding as further described herein. The no-flow nipple includes a nipple wall forming a tip portion and a base portion, a nipple cavity defined by the nipple wall, and a flange including an opening to the nipple cavity, where the base portion is intermediate the tip portion and the flange, and the flange is configured for joining the first nipple to a nipple collar. The nipple tip of the no-flow nipple is fully enclosed such that none of a fluid contained in the nipple cavity can flow directly from the nipple cavity through the nipple wall of the tip portion.

In the example provided, a no-flow nipple is modified to provide a flow nipple by forming an aperture in the tip portion of the no-flow nipple such that fluid contained in the nipple cavity can flow directly from the nipple cavity through the nipple wall of the tip portion through the aperture. A plurality of flow nipples is provided, with each flow nipple of the plurality characterized by a different flow rate of fluid through the aperture, where the flow rate corresponds to a cross-sectional area of the aperture. In one example, a first flow nipple is characterized by a first flow rate of fluid through the aperture of the first flow nipple, where the aperture of the first flow nipple has a first cross-sectional area. A second flow nipple is provided and is characterized by a second flow rate of fluid through the aperture of the second flow nipple, where the aperture of the second flow nipple has a second cross-sectional area. A third flow nipple is provided and is characterized by a third flow rate of fluid through the aperture of the third flow nipple, where the aperture of the third flow nipple has a third cross-sectional area. In the present example, the first flow rate is less than the second flow rate, and the third flow rate is greater than the second flow rate. The corresponding cross-sectional areas of the flow nipples are similarly related, with the cross-sectional area of the aperture of the first flow nipple being smaller than the cross-sectional area of the aperture of the second flow nipple, and the cross-section area of the aperture of the third flow nipple being larger than the cross-sectional area of the aperture of the second flow nipple.

In the example provided, a no-flow nipple is modified to provide a bolus delivery nipple by including a bolus delivery conduit disposed within the nipple cavity of the no-flow nipple. The bolus delivery conduit includes a conduit intake and a conduit outlet, where the conduit outlet is attached to the nipple wall such that fluid received into the bolus delivery conduit via the conduit intake can flow through the bolus delivery conduit and be outputted from the nipple as a bolus. The bolus delivery conduit is attached to the nipple wall within the tip portion such that no fluid can flow directly from the nipple cavity through the nipple wall of the tip portion, and as such, the bolus delivery nipple also functions as a no-flow nipple in that none of a fluid contained in the nipple cavity can flow directly from the nipple cavity through the nipple wall of the tip portion. The conduit outlet extends through the nipple wall at an outlet angle relative to the central axis of the nipple, where the outlet angle determines a trajectory of a bolus outputted from the bolus delivery conduit. In one example, the outlet angle is zero and the outlet axis of the conduit outlet is coincident with the central axis. In another example, the conduit outlet is parallel to the central axis. In another example, the conduit outlet is angled relative to the central axis at an outlet angle which is greater than five degrees and less than sixty degrees. The conduit outlet is shaped to form the bolus from fluid received into the bolus delivery conduit, where the conduit outlet can be shaped as one of a slit, oval, or rectangle opening having one of a tapered, straight, or contoured side surface.

In one example, the bolus delivery conduit can be shaped as a catheter tube having a first end attached to the nipple wall in the nipple portion to provide the conduit outlet, and a second end defining the conduit intake. The conduit intake can include an intake coupling to connect an outlet port of a fluid reservoir to the bolus delivery conduit. An actuator can be used to actuate the delivery of a predetermined amount of fluid from the reservoir to the bolus delivery conduit such that the predetermined amount of fluid is outputted from the conduit outlet as the bolus. By way of example, the predetermined amount of fluid can be equivalent to a droplet, where the bolus outputted from the conduit is formed as the droplet. The reservoir and actuator can be configured as a syringe, and the intake coupling configured to receive the syringe.

In one example, the bolus delivery conduit can have a substantially cylindrical shape and be oriented in the nipple cavity in a first example such that the bolus delivery conduit is substantially parallel to a central axis of the bolus delivery nipple. In another example, the bolus delivery conduit can have a substantially cylindrical shape and be angled relative to the central axis to assist flow of fluid through the bolus delivery conduit and formation of the bolus outputted from the conduit outlet. In another example, the bolus delivery conduit can include at least one conduit segment which is oriented at a first conduit angle relative to the central axis and at least one other conduit segment which is oriented at a second conduit angle relative to the central axis. In this example, one of the conduit segments can be substantially parallel to the central axis. The bolus delivery conduit can be formed or molded such that the conduit is integral to the no-flow nipple, for example, the bolus delivery conduit can be formed such that the conduit is contained within and/or connected along at least a portion of its length to the nipple wall, terminating at the conduit intake, where the conduit intake is positioned relative to the nipple base and/or the nipple flange to define a intake coupling for connecting an outlet port in fluid communication with a fluid reservoir to the bolus delivery conduit. The conduit intake of the bolus delivery conduit and the outlet port are configured to interface with each other such that a fluid connection is established between the bolus delivery conduit and the reservoir. In one example, the outlet port interfaces with the conduit intake by insertion of the outlet port into the conduit intake. In one example, the outlet port interfaces with the conduit intake by insertion of the conduit intake into the outlet port.

The system can further comprise a bolus delivery hub which includes an outlet port, where the outlet port is configured to interface with the conduit intake such that the conduit intake is in fluid communication with the reservoir via the outlet port. The bolus delivery hub further comprises an intake port including a reservoir interface to receive fluid into the intake port from the reservoir, where the intake port is in fluid communication with the outlet port. In one example, the outlet port of the bolus delivery hub can be configured such that the outlet port is in fluid communication with a distal hub face of the bolus delivery hub, where the distal hub face is configured such that with the distal hub face in contact with a proximal flange face of the nipple flange of the bolus delivery nipple, the conduit intake is in fluid communication with the outlet port. The bolus delivery hub can further include an intake port including a reservoir interface to receive fluid into the intake port from the reservoir, where the intake port is in fluid communication with the outlet port. The bolus delivery hub can include a hub face which can be positioned in contact with the flange to enclose the nipple cavity such that the reservoir is defined by the nipple cavity, and such that the reservoir interface of the intake port is disposed within the nipple cavity to receive fluid from the reservoir. In one example, the bolus delivery hub includes one or both of the actuator and the reservoir.

The feeding transition system can further include a nipple collar comprising a collar aperture and an interior wall. The interior wall can include a cylindrical surface which may be threaded or otherwise configured to receive a threaded end of an infant nursing bottle, a threaded end of a coupling body of a feeding performance evaluation device, and/or a hub interface the bolus delivery hub, as further described herein. The interior wall can include an annular surface surrounding the collar aperture and intermediate the collar aperture and the cylindrical surface, where the annular surface is configured to interface with the flange of a nipple, where the nipple can be a no-flow nipple, a flow nipple, and/or a bolus delivery nipple. The nipple is joined to the nipple collar such that the base and tip portions of the nipple protrude through the collar aperture and such that the flange portion is retained within the collar in contact with the interior wall. In one example, the nipple joined to the nipple collar is a bolus delivery nipple, and a bolus delivery hub is at least partially disposed within the nipple collar such that the nipple flange is intermediate the bolus delivery hub and the interior wall, and such that the outlet port of the bolus delivery hub interfaces with the conduit intake of the bolus delivery nipple.

The feeding transition system can further include a feeding performance evaluation system comprising a feeding performance evaluation coupling device, where the coupling device is at least partially disposed within the nipple cavity and the feeding performance evaluation apparatus is configured to output a measurement of a tongue movement exerted on the nipple wall. In one example, the feeding performance evaluation coupling device comprises a coupling body having a proximal end and a distal end, where the coupling body includes a central passage extending from the proximal end to the distal end. The coupling device further comprises a lever including a lever end, where the lever is positioned in the central passage and is pivotably connected to the coupling body such that the lever end protrudes from central passage at the distal end of the coupling body. In the example, the coupling body is joined to the nipple flange by the nipple collar such that the lever end is disposed within the nipple cavity and such that the lever is pivoted in response to the tongue movement exerted on the nipple wall. In one example, the nipple is a bolus delivery nipple and the feeding transition system further includes a bolus delivery hub disposed between the flange and the distal end of the coupling body such that the outlet port of the bolus delivery hub interfaces with the conduit intake of the bolus delivery conduit. In another example, the nipple is a bolus delivery nipple and the feeding transition system further includes a bolus delivery hub disposed at the proximal end of the coupling body. In this example, the system further includes a conduit extension comprising a first end and a second end, where the first end is configured to interface with the output port of the bolus delivery hub and the second end is configured to interface with the conduit intake of the bolus delivery nipple. The conduit extension includes a conduit in fluid communication with the first end and the second end. In this example, the conduit extension extends through the central passage such that first end of the conduit extension is interfaced with the outlet port of the bolus delivery hub and the second end of the conduit extension is interfaced with the conduit intake of the bolus delivery nipple, and such that the outlet port of the bolus delivery hub is in fluid communication with the conduit intake of the bolus delivery conduit via the conduit extension.

A method for transitioning an infant subject to oral feeding is provided. The method comprises providing a feeding transition system where the feeding transition system comprises a nipple set including at least one no-flow nipple and at least one flow nipple formed as previously described herein. The method further includes selecting a first nipple from the nipple set, conducting a first feeding session with the infant subject using the first nipple, and determining a first feeding response of the infant subject to the first feeding session. The method further includes selecting, using the first feeding response, a second nipple from the nipple set, where the second nipple is one of the first nipple and another nipple of the nipple set, conducting a second feeding session with the infant subject using the second nipple, and determining a second feeding response of the infant subject to the second feeding session. In one example, the method can include comparing the first and second feeding responses to determine whether a change in oral feeding ability has occurred, and selecting, using the first and second feeding responses, a third nipple from the nipple set, where the third nipple can be one of the first nipple, the second nipple, and another nipple of the nipple set, conducting a third feeding session with the infant subject using the third nipple, and determining a third feeding response of the infant subject to the third feeding session.

In one example, the method includes the at least one no-flow nipple comprises a first no-flow nipple and a second no-flow nipple, where the second no-flow nipple is configured as a bolus delivery nipple constructed as described herein. In another example, the at least one flow nipple of the method a first flow nipple and a second flow nipple, where the first flow nipple is characterized by a first flow rate of fluid through the aperture of the first flow nipple, the second flow nipple is characterized by a second flow rate of fluid through the aperture of the second flow nipple, and the first flow rate is less than the second flow rate. The at least one flow nipple can include a third flow nipple characterized by a third flow rate of fluid through the aperture of the third flow nipple which is the second flow rate of the second flow nipple.

In one example, the method further includes providing a feeding performance evaluation system comprising a feeding performance evaluation coupling device, where the feeding performance evaluation coupling device is at least partially disposed within the nipple cavity and is configured to output a measurement of a tongue movement exerted on the nipple wall by the infant subject. The method further includes collecting at least one measurement of the tongue movement exerted on the nipple wall by the infant subject during the first feeding session, using the feeding performance evaluation coupling device, and determining the first feeding response of the infant subject using the at least one measurement. The coupling device can include a lever including a lever end, where the lever end is disposed within the nipple cavity such that the lever is pivoted in response to the tongue movement exerted on the nipple wall. In this example, the method can further comprise conducting the first feeding session including evaluating the feeding performance of the infant subject using the feeding performance evaluation coupling device.

In one example, the first nipple of the method is configured as a no-flow bolus delivery nipple comprising a bolus delivery conduit including a conduit intake and a conduit outlet, where the bolus delivery conduit is disposed in the nipple cavity of the no-flow nipple, the conduit outlet is attached to the nipple wall such that fluid received into the bolus delivery conduit via the conduit intake can flow through the bolus delivery conduit and be outputted from the nipple as a bolus, and where the bolus delivery conduit is attached to the nipple wall such that no fluid can flow directly from the nipple cavity through the nipple wall of the tip portion. In this example, a reservoir containing a fluid is in fluid communication with the conduit intake, and the system further includes an actuator which is actuable to deliver a predetermined amount of fluid from the reservoir to the bolus delivery conduit such that the predetermined amount of fluid is outputted from the conduit outlet as the bolus. The method further comprises actuating the actuator during the first feeding session to output the bolus to the infant subject, collecting the at least one measurement of the tongue movement exerted on the nipple wall by the infant subject in response to the bolus, using the feeding performance evaluation coupling device, and determining the first feeding response of the infant subject to the bolus using the at least one measurement. In one example, the feeding transition system can further include the actuator and the feeding performance evaluation system in communication such that the actuator is actuable by a signal outputted by the feeding performance evaluation system to the actuator such that the method can further comprise the feeding performance evaluation system outputting the signal to the actuator in response to the at least one measurement of the tongue movement exerted on the nipple wall by the infant subject during the first feeding session.

The above noted and other features and advantages of the present disclosure are readily apparent from the following detailed description when taken in connection with the accompanying drawings.

DESCRIPTION OF THE DRAWINGS

FIG. 8 is a schematic end view in the direction of arrow 8 of FIG. 10, of an example bolus delivery nipple, showing example positioning of the conduit outlet of the bolus delivery nipple of FIG. 10;

FIG. 9 is a schematic cross-sectional view of an example feeding transition mechanism including an example bolus delivery nipple positioned in a nipple collar including cross-section 9-9 of the bolus delivery nipple of FIG. 8;

FIG. 10 is a schematic cross-sectional view of an example bolus delivery nipple including a bolus delivery conduit having a conduit intake and a conduit outlet and showing example positioning of the conduit intake and the conduit outlet;

FIG. 11 is a schematic cross-sectional view of an example bolus delivery nipple;

FIG. 12 is a schematic view of a method for transitioning an infant subject to oral feeding using the nipple set of FIG. 1;

FIG. 13 is a flowchart showing the method for transitioning an infant subject to oral feeding using the nipple set of FIG. 1 and optionally using the feeding performance system shown in FIGS. 17-25;

FIG. 14 is a schematic view of a first example of the method for transitioning an infant subject to oral feeding using the nipple set of FIG. 1;

FIG. 16 is a schematic perspective exploded view of the example feeding transition system of FIG. 15, further including an evaluation device in communication with the coupling device and the bolus delivery hub;

DETAILED DESCRIPTION

Figure 1:
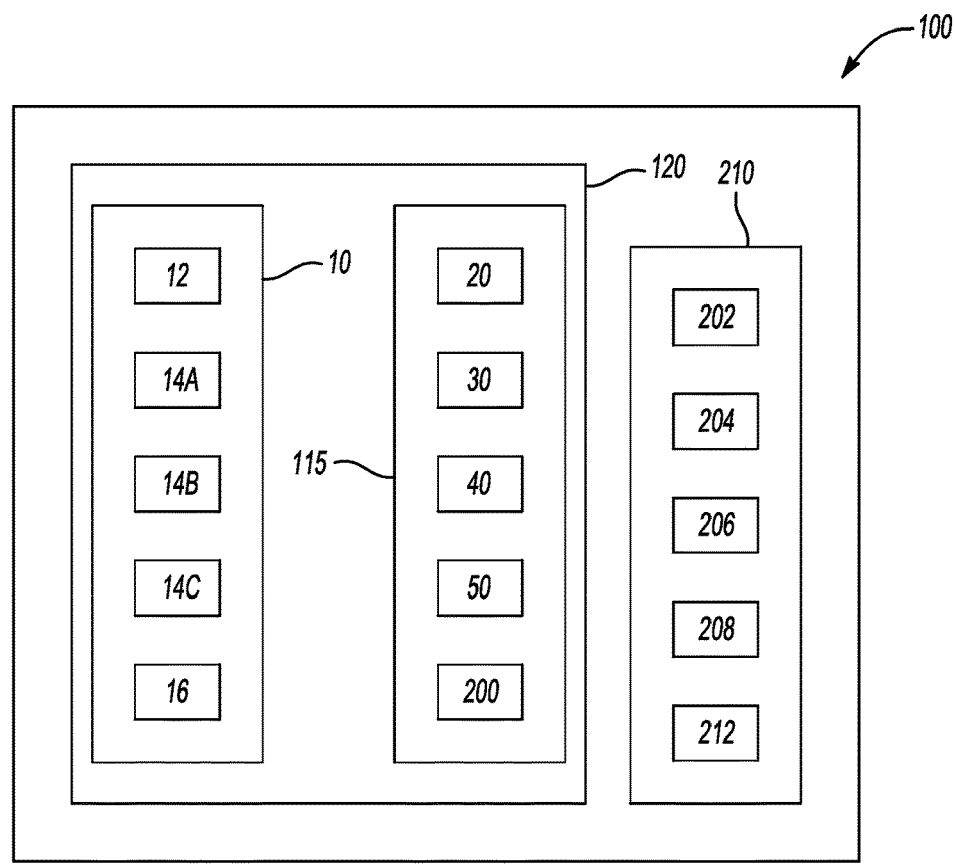
FIG. 1 is a schematic illustration of a feeding transition system for transitioning an infant subject to oral feeding comprising a nipple set including at least one no-flow nipple, a set of mechanism components for forming a feeding transition mechanism including a nipple selected from the nipple set, and an evaluation device.
Figure 2:
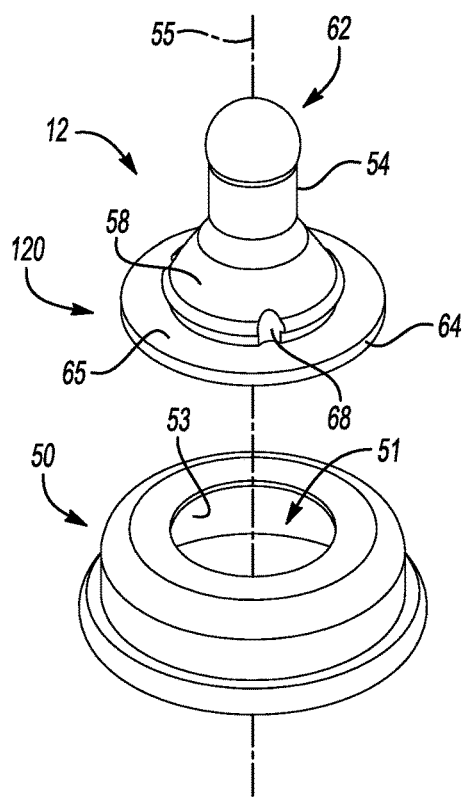
FIG. 2 is a schematic perspective exploded view of a feeding transition mechanism including a no-flow nipple selected from the nipple set of FIG. 1 and a nipple collar from the set of mechanism components of FIG. 1.
Figure 3:
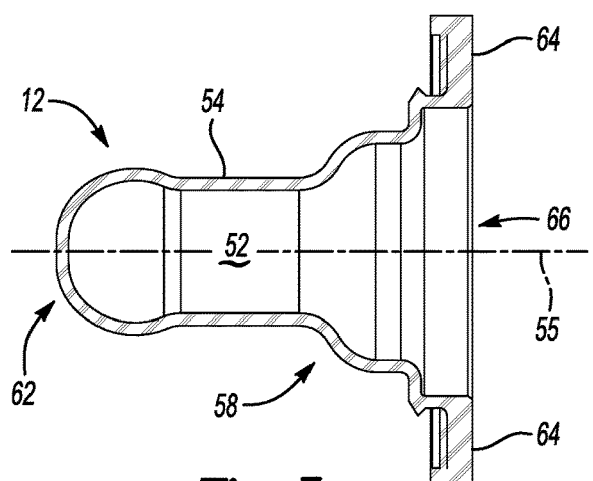
FIG. 3 is a schematic cross-sectional view of the no-flow nipple of FIG. 2.
Figure 4:
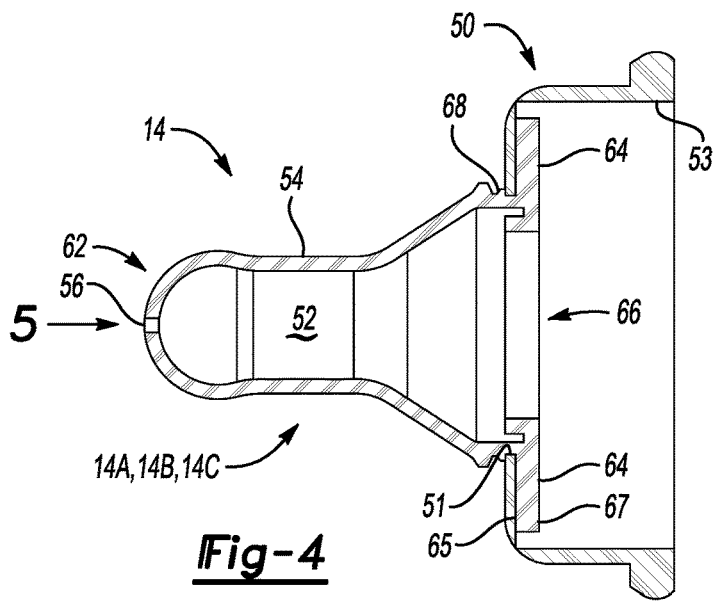
FIG. 4 is a schematic cross-sectional view of an example feeding transition mechanism including a flow nipple and nipple collar of FIG. 1.
Figure 5:
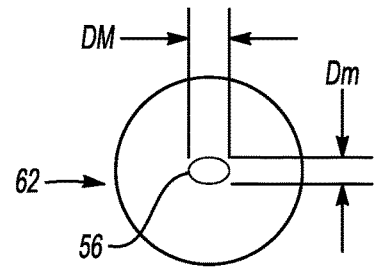
FIG. 5 is a schematic end view in the direction of arrow 5 of FIG. 4, showing a nipple aperture of the flow nipple of FIG. 4.

Providing consistent environmental factors and feeding constructs to an infant can help with the ease of transition of the infant to self-sustained oral feeding. Provided herein are a feeding transition nipple mechanism 120 and system 100 shown in FIG. 1, and a method 105 of use shown in FIG. 18, for transitioning an infant to oral feeding. Referring to the drawings wherein like reference numbers represent like components throughout the several figures, the elements shown in FIGS. 1-18 are not necessarily to scale or proportion. Accordingly, the particular dimensions and applications provided in the drawings presented herein are not to be considered limiting. Referring now to FIG. 1, shown is a feeding transition system 100 including a set of nipples 10, also referred to herein as a nipple set, for use in transitioning an infant subject 60 (see FIGS. 7 and 15) to oral feeding using one or more of the nipples 12, 14A, 14B, 14C, 16 of the nipple set 10, using the method 105 shown in FIG. 18. The nipple set 10, in the illustrative example shown in FIG. 1, includes a no-flow nipple 12, a series of flow nipples 14 (see FIGS. 1 and 6) including flow nipples 14A, 14B, 14C each having a different flow rate (see FIG. 6), and a bolus delivery nipple 16 for actuated delivery of a bolus 36 to an infant subject 60 (see FIGS. 7 and 15) during a feeding session. An infant subject 60 can also be referred to herein as an infant. As shown in FIGS. 2 and 3, the no-flow nipple 12 includes a nipple wall 54 forming a tip portion 62 and a base portion 58, a nipple cavity 52 defined by the nipple wall 54, and a flange 64 including a base opening 66 to the nipple cavity 52, where the base portion 58 is intermediate the tip portion 62 and the flange 64, and the flange 64 is configured for joining the no-flow nipple 12 to a nipple collar 50. The nipple tip 62 of the no-flow nipple 12 is fully enclosed such that none of a fluid contained in the nipple cavity 52 can flow directly from the nipple cavity 52 through the nipple wall 54 of the tip portion 62. The fluid contained in the nipple cavity 52 can be a liquid or gaseous fluid. In the example shown in FIGS. 2 and 3, the fluid contained in the nipple cavity 52 is air. The example is non-limiting, for example, the no-flow nipple 12 can be joined to a fluid reservoir 40 such as a feeding bottle 112 (see FIG. 16) using the nipple collar 50, such that the nipple cavity 52 can be filled with a liquid fluid 44 such as an infant formula, breast milk, water, etc., to provide an infant 60 a sensory experience of a fluid-filled nipple during a transition training session.

Figure 6:
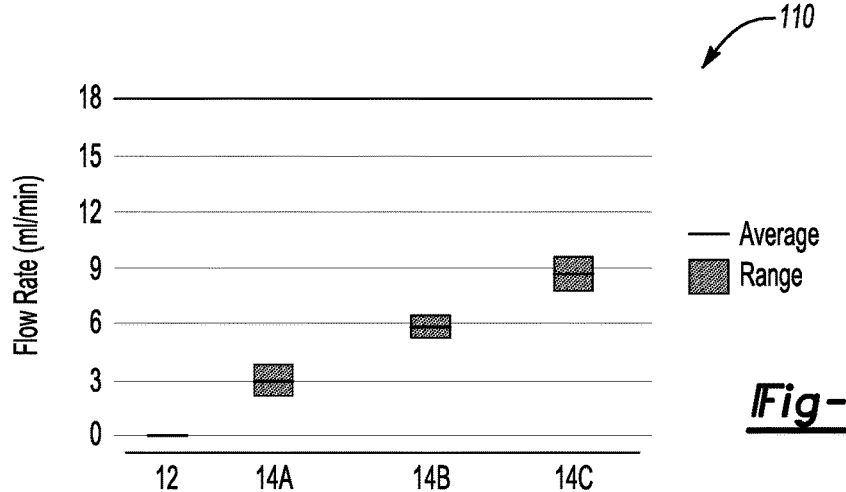
FIG. 6 is a graph showing the range of flow rate for each of a no-flow and a plurality of flow nipples of the nipple set of FIG. 1.

The series of flow nipples 14, in the non-limiting example shown in FIGS. 1 and 6, includes an extra slow flow (ESF) nipple 14A, a slow flow (SLF) nipple 14B, and a standard flow (STF) nipple 14C, where the flow nipples 14A, 14B, 14C can be referred to collectively herein as flow nipples 14, and individually as a flow nipple 14 when generally referring to any one of the plurality of flow nipples 14A, 14B, 14C. The nipples 12, 14A, 14B, 14C, 16 in the nipple set 10 have a similar shape, size, texture and material, to provide a consistent feeding environment to the infant 60 being transitioned to oral feeding using the nipple set 10 with the method 105 described herein. The consistent shape, texture, etc. of the plurality of nipples 12, 14A, 14B, 14C,16 in the nipple set 10, and the use of the no-flow nipple 12 and the bolus delivery nipple 16 for bolus delivery to the infant 60 during training to transition the infant 60 to oral feeding provides consistent feeding environmental factors and consistent feeding constructs, including a consistent nipple sensory experience, which aid in easing transition of the infant 60 to oral feeding. In one example, each of the flow nipples 14A, 14B, 14C and the bolus delivery nipple 16 is formed by modification of a no-flow nipple 12 such that each of the no-flow, flow and bolus delivery nipples 12, 14, 16 have the same exterior shape and size, have the same texture and are made of the same material, to provide a consistent feeding environment to an infant being transitioned to oral feeding using a combination of the no-flow nipple, the flow nipples and/or the bolus delivery nipple with the method of transitioning the infant subject to oral feeding as further described herein.

As an illustrative example, a no-flow nipple 12 can modified as described herein by forming an aperture 56 in the tip portion 62 of the no-flow nipple 12 such that air or liquid fluid contained in the nipple cavity 52 can flow directly from the nipple cavity 52 through the nipple wall 54 of the tip portion 62 through the aperture 56, providing the infant subject 60 using the flow nipple 12 with a sensory experience with the flow nipple 12 which is consistent with the sensory experience provided by a no-flow nipple 12 and/or a bolus delivery nipple 16 of the nipple set 10.

As shown in detail in FIGS. 7-17, the bolus delivery nipple 16 includes a bolus delivery conduit 18 disposed in the nipple cavity 52 and including a conduit outlet 22 formed in the tip portion 62 of the bolus delivery nipple 16 for actuated delivery of a bolus 36 (see FIGS. 7 and 15) during feeding. In the illustrative example shown in FIG. 7, a no-flow nipple 12 is modified to form a bolus delivery nipple 16 by attaching a bolus delivery conduit 18, which can also be referred to herein as a delivery conduit 18, formed of a tubing element, such as catheter tubing, to the nipple wall 54 in the tip portion 62, to form a conduit outlet 22 in the tip portion 62 of the bolus delivery nipple 16. In the illustrative example shown in FIGS. 8-17, a no-flow nipple 12 is modified to form a bolus delivery nipple 16 by molding or otherwise forming a bolus delivery conduit 18 in the nipple cavity 52 such that the bolus delivery conduit 18 is integral to the nipple wall 54. The bolus delivery conduit 18 is attached to the nipple wall 54 within the tip portion 62 such that no fluid can flow directly from the nipple cavity 52 through the nipple wall 54 of the tip portion 62, e.g., the only fluid outputted from the tip portion 62 is the bolus 36 outputted from the conduit 18, and as such, the bolus delivery nipple 16 also functions as a no-flow nipple in that none of a fluid contained in the nipple cavity 52 can flow directly from the nipple cavity 52 through the nipple wall 54 of the tip portion 62 in response to an infant 60 sucking or otherwise exerting a force on the bolus delivery nipple 16. In the examples shown in FIG. 7 and FIGS. 8-17, the delivery conduit 18 is contained with a nipple cavity 52 of the bolus delivery nipple 16 such that the delivery conduit 18 does not interfere with the infant's oral contact with the exterior surface of the bolus delivery nipple 16, and as such provides a sensory experience with the bolus delivery nipple 16 which is consistent with the sensory experience provided by a no-flow nipple 12 and a flow nipple 14, such that the bolus delivery nipple 16 can be used to provide the bolus 36 to the infant 60 within interfering with, but rather supplementing, the infant's development of suck-swallow coordination. As shown in FIGS. 7-17 and described in further detail herein, the delivery conduit 18 is fluidly connected to a reservoir 40 containing a fluid 44, and delivery of the bolus 36 formed of the fluid 44 is actuated by an actuator 30, which may be manually or automatically controlled.

In one example, the feeding transition nipple system 100 provided herein can include and/or be used in conjunction with a feeding performance evaluation system 200 (see FIGS. 1, 16 and 17) having common inventorship with the present disclosure, disclosed in U.S. non-provisional application Ser. No. 14/665,644 filed Mar. 23, 2015 and published as U.S. application 2015/0208979A1 on Jul. 3, 2015, U.S. non-provisional application Ser. No. 14/166,281 filed Jan. 28, 2014 and issued as U.S. Pat. No. 8,986,226 on Mar. 24, 3015, and U.S. non-provisional application Ser. No. 13/479, 640 filed May 24, 2012 and issued as U.S. Pat. No. 8,663, 131 on Mar. 4, 2014, the entire disclosure of each being incorporated by reference herein. In one example, the method 105 shown in FIG. 18, for transitioning an infant 60 to oral feeding, includes using feeding performance information gathered from the feeding performance evaluation system 200 to select a nipple 12, 14, 16 or sequence of nipples from the feeding transition nipple set 10, and to evaluate the infant's response to the selected nipple or sequence of nipples, for example, using the coupling device 70 and/or the evaluation device 210 of the feeding performance evaluation system 200. In an example shown in FIGS. 16 and 17, a bolus delivery apparatus 20 including a bolus delivery nipple 16 and a bolus delivery hub 29 can be integrated with the feeding performance evaluation system 200 such that bolus delivery can be actuated during measurement of and/or in response to the infant's suck-swallow performance as measured and/or evaluated using the feeding performance evaluation system 200.

Referring now to FIG. 1, the feeding transition system 100 includes a nipple set 10 comprising a no-flow nipple 12, a series of flow nipples 14A, 14B, 14C, and a bolus delivery nipple 16. One or more of the nipples 12, 14, 16 can be used during transitioning of an infant 60 to oral feeding, using, for example, the method shown in FIG. 18. A nipple 12, 14, 16 selected from the nipple set 10 can be combined with one or more of mechanism components 115 to form a feeding transition mechanism 120. The mechanism components 115 can include, by way of example, a bolus delivery apparatus 20, an actuator for actuating delivery of a predetermined amount of fluid 44 from a reservoir 40 to a bolus delivery nipple 16, a reservoir 40 for containing the fluid 44, a nipple collar 50 where the selected nipple 12, 14, 16 can be joined to the nipple collar 50 via corresponding interfaces defined by the nipple flange 64 and the interior wall 53 of the nipple collar 50 and insertion of the nipple tip portion 62 and base portion 58 though a collar aperture 51, and a feeding performance evaluation system 200 which can include a coupling device 70 (see FIGS. 15-17) and an evaluation device 210. In one example, the bolus delivery apparatus 20 comprises the bolus delivery nipple 16, the actuator 30, and the reservoir 40, and can further include a bolus delivery hub 29 and/or a collar 50. The interior wall 53 of the nipple collar 50 can include a cylindrical surface which may be threaded or otherwise configured to receive a threaded end of an infant nursing bottle 112, a threaded end of the coupling body 72, and/or a hub interface 23 of the bolus delivery hub 29, as further described herein. The interior wall 53 of the collar 50 can include an annular surface surrounding the collar aperture 51 and which is intermediate the collar aperture 51 and the cylindrical surface of the interior wall 53, where the annular surface is configured to interface with the flange 64 of a nipple 12, 14, 16, where the nipple can be a no-flow nipple 12, a flow nipple 14, and/or a bolus delivery nipple 16. The nipple 12, 14, 16 is joined to the nipple collar 50 such that the base and tip portions 58, 62 of the nipple 12, 14, 16 protrude through the collar aperture 51 and such that the flange portion 64 is retained within the collar and in contact with the interior wall 53. The evaluation device 210 can be used in conjunction with one or both of the feeding transition mechanism 120 and the feeding performance evaluation coupling device 70, to analyze data received form one or both of the mechanism 120 and the coupling device 70 in evaluating the feeding performance of a subject infant 60. For example, the evaluation device 210 can be in communication via a communication interface 212 with a communications interface 32 of an actuator 30 to receive data indicating the actuator 30 has been actuated to release a predetermined amount of fluid to the bolus delivery nipple 16, and/or to send a signal to the actuator 30 to actuate the release of a predetermined amount of fluid 44 to the bolus delivery nipple 16.

As shown in FIGS. 2-4 and FIGS. 7-11, each of the nipples 12, 14, 16 in the nipple set 10 includes a nipple wall 54 forming a base portion 58 and a tip portion 62 which defines a nipple cavity 52 having a central axis 55, and further includes a nipple flange 64 having a distal flange face 65 and a proximal flange face 67. The nipple flange 64 includes a base opening 66, through which the nipple cavity 52 is accessible from the proximal flange face 67, such that fluid 44 can flow into the nipple cavity 52 through the base opening 66. Each of the nipples 12, 14, 16 can include a vent 68, for venting the nipple during feeding to allow an ingress of air for pressure balancing in the nipple cavity 52. The no-flow nipple 12 is characterized by a tip portion 62 which is fully enclosed, e.g., there is no aperture 56 in the tip portion 62 through which fluid contained in the nipple cavity 52 can pass from the nipple cavity 52 to the exterior of the tip portion 62. As such, the flow rate of a no-flow nipple 12 of fluid from the nipple cavity 52 is zero, as indicated by the graph shown in FIG. 6. The no-flow nipple 12 can be used to familiarize an infant 60 with the feel, shape and size of a nipple, and to condition an infant 60 to respond to the introduction of a nipple including developing the infant's suck-swallow-breathe ability, for example, prior to the infant 60 being cleared, e.g., released, for oral feeding. Using a no-flow nipple 12 which is has the same texture, material, feel, shape, etc. as a flow nipple 14 for conditioning the infant provides a consistent feeding environmental factors and consistent feeding constructs which aid in easing transition of the infant 60 to oral feeding, and as such, a no-flow nipple 12 provides an advantage relative to, for example, a pacifier. Consistency in feeding environment factors and feeding constructs with a flow nipple 14 would not be provided by a pacifier, which does not fully replicate a flow nipple 14 as does the no-flow nipple 12. The no-flow nipple 12 can be used with and without fluid in the nipple cavity 52, for different resistances of the no-flow nipple 12. Different fluids can be used in the nipple cavity 52 of the no-flow nipple 12 to provide different resistances, including, for example, using water and/or formula as a fluid, to an infant 60 during a training session using a fluid-filled no-flow nipple 12. The no-flow nipple 12 can be used alternatively with flow nipples 14 and bolus delivery nipple 16, in the course of using method 105 to evaluate and/or to develop the feeding ability of the infant 60, as described further herein.

In the example shown in FIG. 1 and FIGS. 4-6, the nipple set 10 includes a series of flow nipples 14 including flow nipples 14A, 14B and 14C. Flow nipple 14A is identified as an extra slow flow (ESF) nipple including an aperture 56 formed in the tip portion 62 and having a shape and cross-sectional area configured to provide a fluid flow through the aperture at an average rate of 3.0 ml/minute. In the example shown, the aperture 56 is laser cut through the wall 54 of the tip portion 62 of the ESF nipple 14A. A laser is preferably used to form the aperture 56 because of the relatively high repeatability the laser demonstrates in cutting the aperture 56 in the same shape and size from one ESF nipple 14A to the next, such that the range of the size and cross-sectional area of the aperture 56 in a plurality of ESF nipples 14A is minimized, for consistency of performance when using multiple ESF nipples 14A in the feeding transitioning of an infant 60. As illustrated by the schematic end view of the nipple aperture 56 shown in FIG. 5, the laser generated aperture 56 can be oval in shape, characterized by a major diameter DM and a minor diameter Dm, which can be used to calculate the cross-sectional area of the aperture 56. The size (DM, Dm), the cross-sectional area, and the ovality (ratio of DM/Dm) of the aperture 56 can be different for each of the flow nipples 14A, 14B, 14C to generate a different average flow rate for each respective one of the flow nipples 14A, 14B, 14C. In an illustrative example, the flow rate of a statistically significant number of ESF nipples 14A was measured by replicating the flow rate measurement methodology described in Pados BF et al. Am J. Speech- .Lang.Pathol. 2015; 24(4);671-679, and an average flow rate and a flow rate range at 95% confidence was calculated for each of the flow nipples 14A, 14B, 14C and plotted in the flow rate range chart 110 shown in FIG. 6. In the illustrative example, the ESF nipple 14A was characterized by an average flow rate of 3.1 ml/minute, and a flow rate range of 2.2-4.0 ml/minute at 95% confidence. In the illustrative example, the slow flow (SLF) nipple 14B was characterized by an average flow rate of 6.1 ml/minute, and a flow rate range of 5.5-6.7 ml/minute at 95% confidence. In the illustrative example, the standard flow (STF) nipple 14C was characterized by an average flow rate of 8.9 ml/minute, and a flow rate range of 8.0-9.9 ml/minute at 95% confidence. The narrow flow rate ranges described herein for each of the different nipple flow rates, e.g., for each of the ESF, SLF and STF nipples 14A, 14B, 14C are of functional significance to the conditioning method described herein, by providing a consistent and predetermined flow rate within a limited range to which an infant's feeding performance can be correlated. It would be understood that a relatively larger range of flow for nipples in any one of the flow rate categories ESF, SLF, STF could decrease the capability to determine a correlation between an infant's feeding performance and the flow rating of the flow nipple 14 used during a feeding session. As described in further detail herein, the method 105 of transitioning an infant 60 to oral feeding can include selecting one or more of the flow nipples 14A, 14B, 14C for use during infant conditioning, where the flow nipples 14A, 14B, 14C can be selected in order of increasing flow rate, as the infant's ability to orally feed improves, can be varied in order or use, and/or can be used in combination with one or both of a no-flow nipple 12 and a bolus delivery nipple 16, depending on the developmental and conditioning needs of the particular infant 60, and the infant's performance response to a nipple of the selected flow rate.

The example of using a laser to form the aperture 56 in the flow nipple 14 is non-limiting, and it would be understood that other manufacturing methods can be used to form the aperture 56, including cutting, molding, burning, slitting, punching, etc., the tip portion 62 to form the aperture 56. Further, it would be understood that other shapes and configurations of the aperture could be used to provide the flow rate ranges for each of the different flow rates provided by the ESF flow nipple 14A, the SLF flow nipple 14B, and the STF flow nipple 14C, including, for example, rectangular apertures, apertures comprising one or more slits, apertures including a plurality of openings which may be of various sizes and distributed to provide the selected flow rate, etc. In an illustrative example, the nipples 12, 14, 16 are made of one or a combination of silicone, rubber, plastic or polymer-based material, or a combination of these. In one example, the nipples 12, 14, 16 are made of a silicone material.

Each of the nipples 12, 14A, 14B, 14C can be inserted into a respective collar 50 which is uniquely colored to add in identification of the flow rating of the particular nipple 12, 14 inserted in the respective collar 50. For example, the no-flow nipple 12 can be inserted into a silver-colored collar 50, the ESF nipple 14A can be inserted into a gold-colored collar 50, the SLF nipple 14B can be inserted into a purple-colored collar, and the STF nipple 14C can be inserted into a white-colored collar 50D to provide a visual identifier of the flow rating of each of the nipples 12, 14A, 14B, 14C, for the convenience of the user in identifying and selecting a particular one of the nipples 12, 14A, 14B, and 14C for use in a particular feeding or training session during transitioning of the infant to oral feeding. In a non-limiting example, the collar 50 is molded from a polymer-based material to which a colorant additive can be added to provide the identifying color of the collar 50 used for each of the nipples 12, 14A, 14B, and 14C. It would be understood that the example provided herein is non-limiting, and that other methods of visually identifying the flow rate of each of the nipples 12, 14A, 14B, 14C could be used, including color coding the nipple material for each respective flow rate, providing a different form of visual identification including an identifier such as a mark, label, letter, symbol, bar code, etc. applied to or formed in the nipple 12, 14 or a corresponding collar 50 into which the nipple 12, 14 is inserted.

As shown in FIGS. 1 and 7-17, the example nipple set 10 further includes a bolus delivery nipple 16, which can also be characterized as a no-flow nipple, since passage a fluid through the nipple wall 54 is limited to outputting of a bolus 36 from the bolus delivery conduit 18 via the conduit outlet 22, where the conduit 18 is sealed from the nipple cavity 52 such that no fluid can flow directly from the nipple cavity 52 through the nipple wall 54 of the tip portion 62. The bolus delivery nipple 16, in the example shown in FIG. 1, includes a delivery conduit 18 having a conduit outlet 22 and a conduit intake 24. In the example shown in FIG. 7, the delivery conduit 18 protrudes through the nipple wall 54 within the tip portion 62 such that fluid 44 can flow through the delivery conduit 18 and can be outputted from the conduit outlet 22 as a bolus 36. The delivery conduit 18 includes a conduit intake 24 for receiving a fluid 44 from a reservoir 40 (see FIGS. 7 and 8), and a conduit outlet 22 for outputting a bolus 36 (see FIGS. 7 and 8). The bolus 36 can include one or more bolus drops 38. In one example, the delivery conduit 18 can be a catheter tube, where the diameter of the catheter tube can be selected to control the size of the bolus drop 38 to be outputted from the delivery conduit 18. In the example shown in FIG. 7, the delivery conduit 18 can be a catheter tube which is inserted into the nipple cavity 52 of a flow nipple 14, via a base opening 66 of the flow nipple 14, and disposed inside the nipple cavity 52 such that conduit outlet 22 extends through the aperture 56 and outward from the exterior surface of the nipple tip portion 62 to form the bolus delivery nipple 16, as shown in detail in FIG. 7. By containing the delivery conduit 18 within the nipple cavity 52, the infant subject 60 can make direct contact with the nipple wall 54 during a feeding session without interference from a bolus catheter, such that the texture, feel, shape, size, etc. of the nipple 16 as sensed by the infant 60 is unaffected by the presence of the delivery conduit 18, and consistent with the texture, feel, shape, size, etc. of other nipples 12, 14 which may be used in conditioning and feeding sessions with that infant 60. As noted previously, providing consistency in feeding environmental factors and feeding constructs, such as consistency in nipple texture, feel, shape, size, etc. while having the ability to vary flow rate from no flow to standard flow and/or provide bolus feeding, by using the nipple set 10 described herein provides an advantage to the infant 60 in transitioning to oral feeding.

Figure 12:
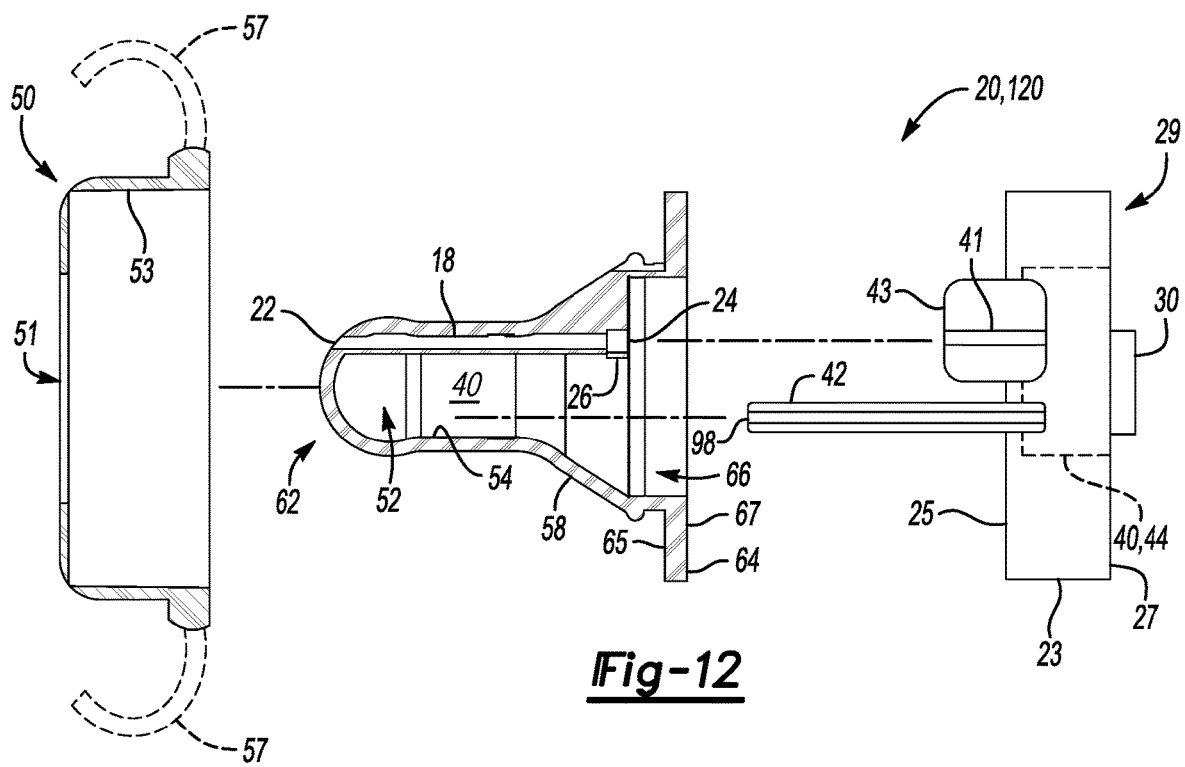
FIG. 12 is a schematic cross-sectional exploded view of an example feeding transition system comprising an example feeding transition mechanism including an example bolus delivery nipple and an example nipple collar including a grasping element; and an example bolus delivery apparatus including the example bolus delivery nipple and an example bolus delivery hub including a fluid reservoir and an actuator for actuating delivery of a bolus via the bolus delivery nipple.

The length of the delivery conduit 18 can be varied as needed to fluidly connect the conduit intake 24 of the delivery conduit 18 to a fluid reservoir 40 containing the fluid 44 to be outputted via the delivery conduit 18 as a bolus 36. The fluid reservoir 40 can be of any configuration suitable for storing and providing the bolus fluid 44 to the delivery conduit 18. In the example shown in FIG. 7, the reservoir 40 can be configured as a syringe which is marked with measurement increments such that the amount of bolus fluid 44 in the reservoir 40, and the amount of bolus fluid 44 discharged from the reservoir 40 to the delivery conduit 18, can be measured and recorded. In the example, the delivery conduit 18 includes an intake coupling 26 attached to the conduit intake 24 to receive the syringe reservoir 40. Other examples of a reservoir 40 to store the bolus fluid 44 can include a fluid cavity of a bottle 112 which can be attached to the collar 50, a reservoir 40 formed by the nipple cavity 52 (see FIG. 12), a retaining pool loaded by syringe, a reservoir 40 contained within a bolus delivery hub 29 (see FIGS. 12 and 13), etc. As shown in FIG. 12, the collar 50 can include one or more grasping elements 57 to enable single-hand use of the bolus delivery apparatus 20. For example, referring to FIGS. 7 and 12, the user can use one or two fingers of the user's hand and the grasping elements 57 to hold the bolus delivery apparatus 20 in position in the mouth of the infant 60 while using a thumb and/or another finger of the user's hand to actuate the actuator 30 to output the bolus 36 from the conduit outlet 22.

Figure 7:
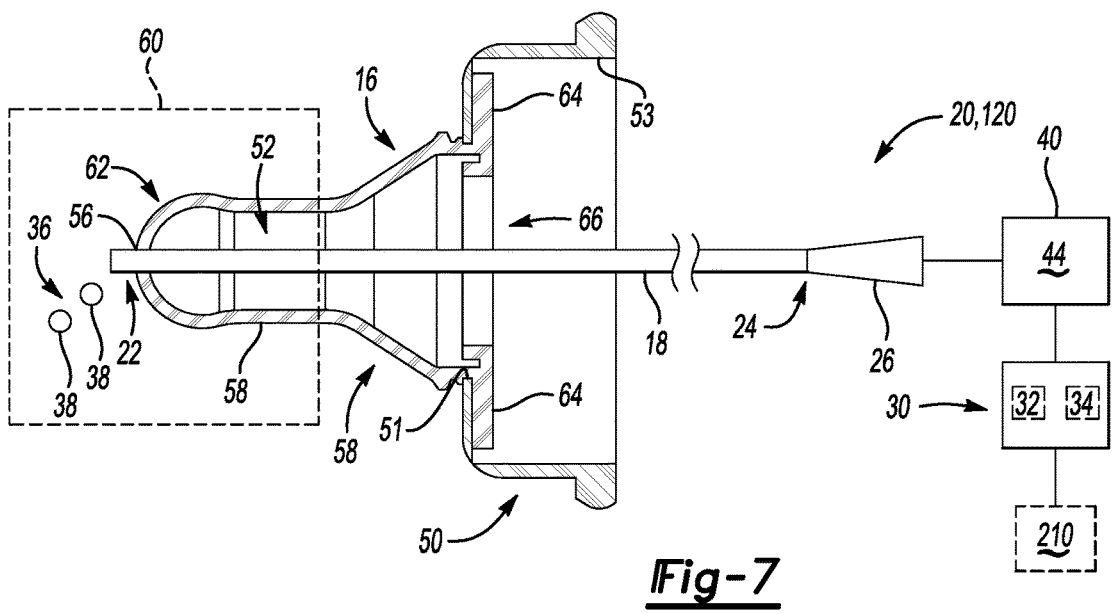
FIG. 7 is a schematic view of an example feeding transition system including an example bolus delivery nipple selected from the nipple set of FIG. 1 positioned in a nipple collar, showing a cross-sectional view of the bolus delivery nipple including a bolus delivery conduit in fluid communication with a fluid reservoir, an actuator for actuating delivery of a bolus via the bolus delivery nipple, and an optional feeding evaluation device.

The example shown in FIG. 7 is not limiting, and other configurations of the delivery conduit 18 can be used. For example, the conduit outlet 22 of the delivery conduit 18 can be positioned in the aperture 56 such that the conduit outlet 22 is flush or nearly flush with the exterior surface of the nipple tip portion 62 and blocks fluid in the nipple cavity 52 from flowing through the aperture 56 to provide a bolus delivery nipple 16. The delivery conduit 18 can be attached to the nipple wall 54 to maintain the position of the delivery conduit 18 in the nipple cavity 52 and/or the position of the conduit outlet 22 relative to the aperture 56, for example, to maintain the conduit outlet 22 flush or nearly flush with the exterior surface of the nipple tip portion 62 of the flow nipple 14.

In another example, as illustrated by FIGS. 8-11, a no-flow nipple 12 can be modified to form a bolus delivery nipple 16 by molding or otherwise attaching or adhering a rib including a delivery conduit 18 to the nipple wall 54 within the nipple cavity 52. The conduit outlet 22 formed through the nipple wall 54 in the tip portion 62 can be formed during molding of the delivery conduit 18, and/or may be formed and/or shaped for example by a material removal process such as laser cutting, to a desired shape, size, and conduit outlet angle. The conduit intake 24 and/or an intake coupling 26 defined by the conduit intake 24 can be formed during molding of the delivery conduit 18 and/or may be formed and/or shaped, for example, by a material removal process such as laser cutting to form the conduit intake 22 and/or the intake coupling 26. The examples are non-limiting, and it would be understood that other means for forming the delivery conduit 18, the conduit outlet 22, the conduit intake 24 and/or the intake coupling 26 can be used such as installing a tubular insert into the rib portion to form the delivery conduit 18, conduit intake 24 and/or intake coupling 26, and/or using a material removal process to form the delivery conduit 18. In one example, the bolus delivery nipple 16 is formed by molding such that the delivery conduit 18 is integral to the bolus delivery nipple 16, e.g., is a continuous part of the bolus delivery nipple 16.

In the example shown in FIG. 9, the delivery conduit 18 can be disposed in a longitudinal (relative to the central axis 55) section or rib protruding from the nipple wall 54 into the nipple cavity 52, where the delivery conduit 18 is contained with the rib or longitudinal section, where the delivery conduit 18 is shaped as a substantially linear cylinder defining a conduit axis 19. In the example shown in FIG. 9, the conduit axis 19 is substantially parallel to the central axis 66 of the bolus delivery nipple such that a conduit angle 31 (see FIG. 11) of the delivery conduit shown in FIG. 9 is zero. In an example shown in FIG. 11, the delivery conduit 18 is non-linear, including a first conduit segment 18a which is parallel to the central axis 55, and a second conduit segment 18b having a conduit axis 19 such that the second conduit segment 18b is sloped at an angle 31 relative to the central axis 55 of the bolus delivery nipple 16. The linearity and/or the slope or angle of the conduit 18 or one or more conduit segments 18a, 18b thereof can be configured to generate a predetermined set of flow characteristics of the fluid 44 as it flows through the delivery conduit 18, including, for example, flow characteristics as required to form and output a bolus 36 of a predetermined size and shape from the conduit outlet 22. The examples shown in the figures are non-limiting, such that other configurations of the delivery conduit 18 can be used, including a delivery conduit 18 which is one of linear, non-linear, and curvilinear, and which is one of parallel to the central axis 55 having a conduit angle 31 of zero, and non-parallel to the central axis having a conduit angle which is non-zero. By way of example, the conduit angle 31 of the delivery conduit 18 and/or the conduit angle 31 of a conduit segment 18a, 18b can be, for example, zero degrees (0°), from about 0° to about 1°, from about 0° to about 3°, from about 0° to about 5°, from about 0° to about 10°, from about 0° to about 15°, from about 0° to about 20°, from about 0° to about 25°, from about 0° to about 30°, from about 0° to about 35°, from about 0° to about 40°, from about 0° to about 45°, from about 1° to about 10°, from about 3° to about 15°, from about 5° to about 30°, from about 10° to about 45°, or from about 3° to about 45°.

Figure 14:
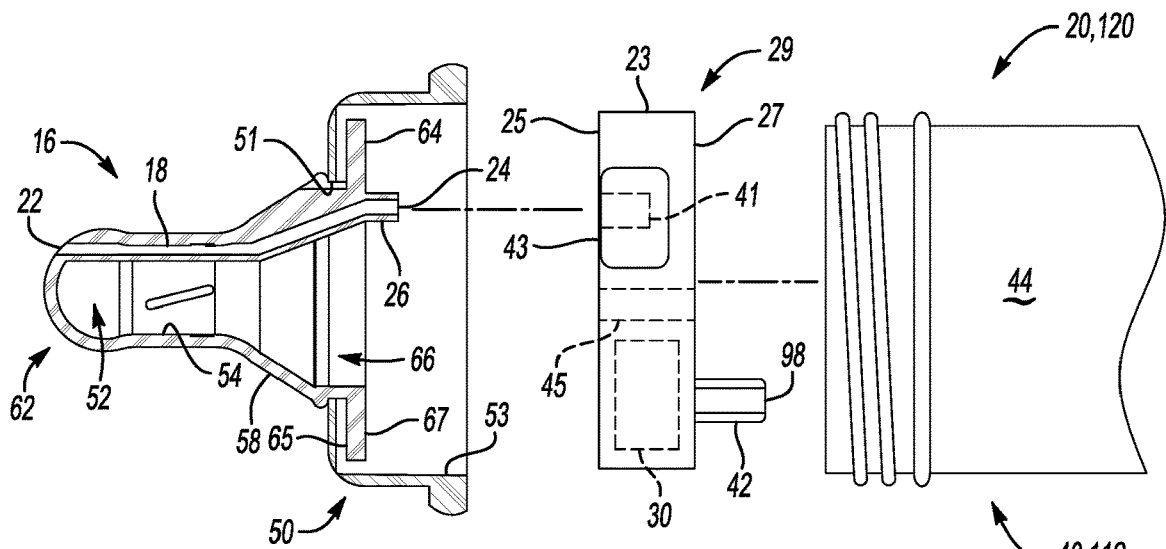
FIG. 14 is a schematic cross-sectional exploded view of an example feeding transition system comprising an example feeding transition mechanism including the example bolus delivery nipple of FIG. 12 and an example nipple collar; and an example bolus delivery apparatus including the example bolus delivery nipple, a fluid reservoir, and an example bolus delivery hub including an actuator for actuating delivery of a bolus via the bolus delivery nipple.

As shown in FIGS. 8-11 and FIG. 14, the delivery conduit 18 terminates at a conduit intake 24 which can define an intake coupling 26. The conduit intake 24 and/or the intake coupling 26 are shaped and/or sized to interface with an output port 42 having a conduit interface 43 such that fluid can be flowed into the delivery conduit 18 from a reservoir 40 via the output port 41 and conduit intake 24 when the conduit interface 43 is interfaced with the intake coupling 26. The conduit intake 24 and/or the intake coupling 26 are positioned proximate the base opening 66 and the flange 64 of the bolus delivery nipple 16, where the conduit intake 24 and/or the intake coupling 26 is located as required to interface the intake coupling 26 with the conduit interface 43. For illustrative purposes, the area proximate the base opening 66 and the flange 64 of the bolus delivery nipple 16 can be divided into zones a, b, c, d, e shown in FIG. 10, where the delivery conduit 18 can be configured such that the conduit intake 24 terminates at an axial and radial location in the one of the zones a, b, c, d, e, as required to interface with the corresponding outlet port 41 forming the bolus delivery apparatus 20. For example, zone a includes an area which immediately adjacent to a proximal flange face 67 of the nipple flange 64 and which extends proximally for an axial distance from the proximal flange face 67, as shown in FIG. 10, such that such that a conduit intake 24 which terminates in zone a is protrudes proximally, from the proximal flange face 67 and outside of the nipple cavity 52. For example, FIG. 14 illustrates an example bolus delivery nipple 16 including a conduit intake 24 terminating at an axial location in zone a which is proximal of the proximal flange face 67, and at a radial location in zone a which aligns radially the inner surface of the flange 64.

For example, zone b includes an area which is distal to and immediately adjacent to and/or flush with a proximal flange face 67 of the nipple flange 64 and which extends distally to a plane including the distal face 65 of the flange 64, such that a conduit intake 24 which terminates in zone b is located axially, relative to the central axis 55 of the bolus delivery nipple 16, between the distal and proximal flange faces 65, 67 of the nipple flange 64. For example, FIG. 11 illustrates an example bolus delivery nipple 16 including a conduit intake 24 terminating at an axial location in zone b which is flush with the proximal flange face 67, and a radial location in zone b which is substantially in radial alignment with the inner surface of the flange 64. For example, zone c includes a radial area which extends proximally to the distal face 65 of the flange 64 and which extends distally to a plane including the proximal end of the base portion 58 of the bolus delivery nipple 16, as shown in FIG. 10. For example, zone d extends axially between the proximal end of the base portion 58 and an axial midpoint of the base portion 58. For example, FIGS. 9 and 12 illustrate an example bolus delivery nipple 16 including a conduit intake 24 terminating at an axial location in zone d which is recessed into the nipple cavity 52 to the proximal end of the base portion 58. For example, zone e includes a radial area which extends between the distal end of the base portion 58 and an axial midpoint of the base portion 58 of the bolus delivery nipple 16, as shown in FIG. 10.

As shown in FIGS. 8-11, the delivery conduit 18 includes a conduit outlet 22 configured to output a bolus 36 from the nipple tip 62 when the bolus delivery apparatus 20 is actuated by the actuator 30. The conduit outlet 22 is shaped and/or sized to form the bolus 36 from fluid 44 received into the bolus delivery conduit 18, where the conduit outlet 22 can be shaped as one of a slit, oval, or rectangle opening having one of a tapered, straight, or contoured side surface defining the opening of the conduit outlet 22. As shown in FIG. 11, the conduit outlet 22 extends through the nipple wall 54 at an outlet angle 21 defined by an outlet axis 59 relative to the central axis 55 of the bolus delivery nipple 16, where the outlet angle 21 is one of a plurality of factors determining a trajectory of a bolus 36 outputted from the bolus delivery conduit 18 via the conduit outlet 22. By way of example, the trajectory of the bolus 36 outputted from the conduit outlet 22 can be determined by a combination of factors which can include at least two of the outlet angle 21, the size and shape of the conduit outlet 22, the velocity of the bolus droplet 38 as it is expelled from the conduit outlet 22, the conduit angle 31, the flow characteristics of the fluid 44 in the delivery conduit 18, the volume and mass of the bolus droplet, and/or the annular location of the conduit outlet 22 on the tip portion 62 within one of a plurality of concentric annular areas x, y, z on the tip portion 62. In the example shown in FIGS. 7 and 9, the outlet angle 21 is zero degrees (0°) relative to the central axis 55. Referring to FIG. 7, in the example shown, the outlet axis 59 of the conduit outlet 22, the conduit axis 19 of the conduit 18 and the central axis 55 are coincident such that the bolus 36 is outputted from the conduit outlet 22 with an initial trajectory defined by the central axis 55 and the annular location of the conduit outlet 22 in a first (central) annular area x on the nipple tip portion 62, such that the bolus 36 in this example is outputted with minimal upward trajectory. In the example shown in FIGS. 8 and 9, the outlet axis 59 and the conduit axis 19 are coincident and the conduit outlet 22 is located in a second (intermediate) annular area y on the tip portion 62 such that the bolus 36 is outputted from the conduit outlet 22 with an initial trajectory defined by the conduit axis 19 and the conduit angle 31 of the delivery conduit 18. In the example shown in FIGS. 8 and 9, the conduit axis 19 is substantially parallel to the central axis 55 such that the conduit angle 31 is about zero degrees (0°), and such that the bolus 36 in this example is outputted with minimal upward trajectory. In one example, the outlet axis 59 and the conduit axis 19 are substantially the same and are each less than ten degrees (10°). An outlet angle less than ten degrees (10°) which causes an initial trajectory of the bolus 36 along the central axis 55 as it is outputted from the conduit outlet 22 may be desirable for strengthening the swallowing reflect of the infant 60, as the bolus 36 is initially directed toward the back of the throat of the infant 60.

In another example shown in FIG. 11, the outlet axis 59 is at an outlet angle 21 of about 45°, such that the bolus 36 in this example is outputted with an initial upward trajectory, e.g., toward the roof of oral cavity of the infant 60. An outlet angle greater than zero degrees (0°) which causes an initial upward trajectory of the bolus 36 as it is outputted from the conduit outlet 22 may be desirable for training the infant 60 to swallow, as the bolus 36 is initially directed away from the throat of the infant 60 and/or toward the cheek and/or upper palate of the oral cavity of the infant 60 such that streaming of the bolus 36 to the back of the throat is avoided. In one example, the conduit outlet 22 is angled relative to the central axis 55 at an outlet angle 21 which is greater than zero degrees (0°) and less than ninety degrees (90°). In one example, the conduit outlet 22 is angled relative to the central axis 55 at an outlet angle 21 which is greater than 30 degrees (30°) and less than 120°. In another example, the conduit outlet 22 is angled relative to the central axis 55 at an outlet angle 21 which is greater than 255° and less than 360° such that the initial upward trajectory of the bolus 36 as it is outputted from the conduit outlet 22 is away from the throat of the infant 60 and/or toward the surface of the tip portion 62, such that bolus 36 disperses within the oral cavity of the infant 60 and generates a taste response in the infant 60.

The examples described herein are not limiting, such that, by way of example, the outlet angle 21 of the conduit outlet 22 can be, for example, zero degrees (0°), from about 0° to about 5°, from about 0° to about 10°, from about 0° to about 30°, from about 0° to about 45°, from about 0° to about 60°, from about 0° to about 75°, from about 0° to about 90°, from about 5° to about 30°, from about 5° to about 45°, from about 5° to about 60°, from about 5° to about 75°, from about 10° to about 30°, from about 10° to about 45°, from about 10° to about 60°, from about 20° to about 60°, from about 30° to about 90°, from about 240° to about 270°, from about 240° to about 300°, from about 240° to about 330°, from about 240° to about 360°, from about 255° to about 270°, from about 255° to about 300°, from about 255° to about 330°, from about 255° to about 355°, from about 255° to about 360°, from about 270° to about 300°, from about 270° to about 330°, from about 270° to about 355°, from about 270° to about 360°, from about 300° to about 330°, from about 300° to about 355°, or from about 300° to about 360°.

As previously described herein, the trajectory of the bolus 36 outputted from the conduit outlet 22 can be determined by a combination of factors which can include a annular location of the conduit outlet 22 on the tip portion 62, relative to a spherical center 63 of the tip portion 62 and the central axis 55 of the bolus delivery nipple, within one of a plurality of concentric annular areas x, y, z on the tip portion 62 as shown in FIGS. 8 and 10. For simplicity of illustration, the tip portion 62 is divided into three annular areas x, y, z, however it would be understood that the tip portion 62 could be divided into a lesser or greater number of concentric annular areas and/or the annular location of the conduit outlet 22 relative to a spherical center 63 of the tip portion 62 and the central axis 55 of the bolus delivery nipple 16 could be expressed as a discrete angular value determined relative to the spherical center 63 of the tip portion 62 and the central axis 55. In the example shown in FIGS. 8-10 a central annular area x has an outer diameter defined by a cone projected from the spherical center 63 having a cone half-angle of x as shown in FIGS. 8 and 10. An intermediate annular area y is bounded by an outer diameter defined by a cone projected from the spherical center 63 having a cone half-angle of (x+y), and bounded by an inner diameter defined by the cone having a cone half-angle of x. Likewise, an outermost annular area z is bounded by an outer diameter defined by a cone projected from the spherical center 63 having a cone half-angle of (x+y+z), where the cones are concentric to the central axis 55 such that the annular areas x, y, z are concentric. In one example, the outer diameters of the annular areas x, y, z are defined, respectively, by cone half-angles of 30, 60 and 90 degrees. In the example shown in FIG. 7, the outlet axis 59 of the conduit outlet 22, the conduit axis 19 of the conduit 18 and the central axis 55 are coincident such that the bolus 36 is outputted from the conduit outlet 22 having an annular location within the central annular area x on the nipple tip portion 62, such that the bolus 36 in this example is outputted with minimal upward trajectory. In the example shown in FIGS. 8 and 9, the conduit outlet 22 is located in the intermediate annular area y on the tip portion 62. The examples are non-limiting, such that a bolus deliver nipple 16 can be configured to include a conduit outlet 22 having an annular location in any one of the central, intermediate, and outermost annular areas x, y, z, as indicated to output a bolus 36 having the characteristics desired for conducting a feeding transition session with an infant subject 60.

In the examples shown in FIGS. 8-17 the conduit outlet 22 is located on the tip portion 62 such that the delivery conduit 18 terminates at the conduit outlet 22, such that in the examples shown, the conduit outlet 22 is located at an end of the delivery conduit 18. The examples are non-limiting, and other configurations can be used, including locating the conduit outlet 22 in an intermediate location along the length of the delivery conduit 18, such that the conduit outlet 22 is located away from the end of the delivery conduit 18. In one example, the end of the delivery conduit 18 terminates at the nipple wall 54, and the conduit outlet 22 is located proximally away from the end of the delivery conduit 18 on the tip portion 62. Locating the conduit outlet 22 in an intermediate location along the length of the delivery conduit 18 affects the fluid flow dynamics of the fluid 44 in the delivery conduit 18 and as the fluid is outputted from the conduit outlet 22, and can affect bolus formation at the conduit outlet 22, to generate a bolus 36 having one or more characteristics, for example, droplet shape, droplet size, initial output trajectory, dispersion pattern, etc. determined by the intermediate location of the conduit outlet 22 relative to the delivery conduit 18. In one example, an intermediate location of the conduit outlet 22 can be utilized to output the bolus 36 in a direction away from the throat of the infant 60, for example, toward the cheek of the infant 60.

Referring now to the examples shown in FIGS. 12-17, in each of the examples shown the bolus delivery apparatus 20 includes a bolus delivery nipple 16, an actuator 30, a reservoir 40, and a bolus delivery hub 29. The bolus delivery hub 29 includes an outlet port 42, where the outlet port 42 can include a conduit interface 43 configured to interface with the intake coupling 26 of the conduit intake 24 such that the conduit intake 24 is in fluid communication with the reservoir 40 via the outlet port 41. The bolus delivery hub 29 further comprises an intake port 42 including a reservoir interface 98 to receive fluid 44 into the intake port 42 from the reservoir 40, where the intake port 42 is in fluid communication with the outlet port 41. In one example, the outlet port 41 of the bolus delivery hub 29 can be configured such that the outlet port 41 is in fluid communication with a distal hub face 25 of the bolus delivery hub 29, where the distal hub face 25 is configured such that, with the distal hub face 25 in contact with a proximal flange face 67 of the nipple flange 64 of the bolus delivery nipple 16, the conduit intake 24 is in fluid communication with the outlet port 41.

In the example shown in FIG. 12, the bolus delivery hub 29 can include a distal hub face 25 which can be positioned in contact with the proximal flange face 67 of the flange 64 to enclose the nipple cavity 52 such that the reservoir 40 is at least partially defined by the nipple cavity 52, and such that the reservoir interface 98 of the intake port 42 is disposed within the nipple cavity 52 to receive fluid 44 from the reservoir 40. In the example shown, the bolus delivery hub 29 includes the actuator 30 and a reservoir 40 where the intake port 42 and the actuator 30 are arranged such that the nipple cavity 52 can be filled with a fluid 44 to provide a reservoir 40 defined by the nipple cavity 52. The fluid 44 in the nipple cavity 52 can be taken up by, e.g., collected by the intake port 42 from the nipple cavity 52 via the reservoir interface end 98 and discharged to the delivery conduit 18 via the interface between the outlet port 41 and the conduit intake 24, and outputted as a bolus 36 from the conduit outlet 22. In the example shown, the bolus delivery hub 29 includes an outlet port 41 in fluid communication with the distal hub face 25, and the bolus delivery nipple 16 includes a conduit intake 24 in fluid communication with the base opening 66 of the nipple cavity 52 such that, with the distal hub face 25 contacting the proximal flange face 67 of the bolus delivery nipple 16, the outlet port 41 aligns and interfaces with the conduit intake 24 by direct contact of the conduit intake 24 with the outlet port 41, and such that the reservoir 40 is in fluid communication with the delivery conduit 18 via the interface formed by the direct contact and alignment of the conduit intake 24 and the outlet port 41. In the example shown, actuation of the actuator 30 causes the fluid 44 present in the nipple cavity 52 to be collected from the nipple cavity via the reservoir interface 98 of the intake port 42, for discharge as a bolus 36 via the delivery conduit 18. The example bolus delivery apparatus 20 shown in FIG. 12 is compactly configured by using the nipple cavity 52 as the reservoir 40, where the base opening 66 of the bolus delivery nipple 16 can be fluidly enclosed by the bolus delivery hub 29.

Figure 13:
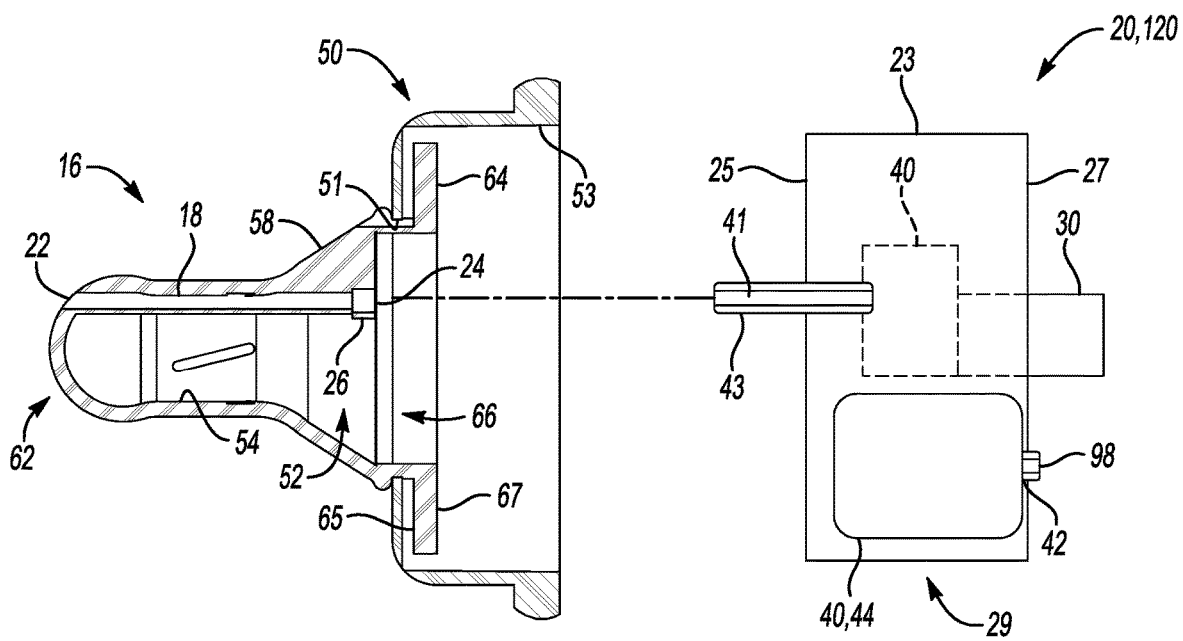
FIG. 13 is a schematic cross-sectional exploded view of an example feeding transition system comprising an example feeding transition mechanism including the example bolus delivery nipple of FIG. 12 and an example nipple collar; and an example bolus delivery apparatus including the example bolus delivery nipple and an example bolus delivery hub including a fluid reservoir and an actuator for actuating delivery of a bolus via the bolus delivery nipple.

In the example shown in FIG. 13, the bolus delivery hub 29 includes an actuator 30 and an intake port 42 in fluid communication with a reservoir 40 contained within the bolus delivery hub 29. In the example shown, the intake port 42 is positioned on a proximal hub face 27 of the bolus delivery hub 29 however this example is non-limiting and the intake port 42 can be positioned elsewhere on the bolus delivery hub 29 as required to position the reservoir interface 98 in fluid communication with a fluid source for filling the reservoir 40 contained in the bolus delivery hub 40. In one example, the reservoir interface 98 can be configured to receive fluid 44 from a syringe, a vial, a feeding bottle 112, or other fluid source. In the example shown, the outlet port 41 protrudes from a distal hub face 25 of the bolus delivery hub 29 and includes a conduit interface 43 which is insertable into the conduit intake 24 to establish a fluid connection between the reservoir 40 and the delivery conduit 18, and such that the outlet port 41 interfaces with the conduit intake 24 by insertion of the outlet port 41 into the conduit intake 24.

In the example shown in FIG. 14, the bolus delivery hub 29 includes an actuator 30 and an intake port 42 configured to receive fluid 44 from a reservoir 40 where the reservoir 40 in the example shown can be selectively positioned such that the reservoir interface 98 can take up fluid 44 from the reservoir 40. In the example shown in FIG. 14, the reservoir 40 is configured as an infant feeding bottle 112 which can be joined by a collar 50 to a bolus delivery nipple 16, where the bolus delivery hub 29 interfaces with the bolus delivery nipple 16 and the reservoir 40 such that the flange 64 of the bolus delivery nipple 16 is disposed between the interior wall 53 of the collar 50 and the distal hub face 25 of the bolus delivery hub 29. In the example shown in FIG. 14, the conduit intake 24 protrudes from a proximal flange face 67 of the bolus delivery nipple 16 and includes a intake coupling 26 which is insertable into the conduit interface 43 of an outlet port 42 located on the distal hub face 25 of the bolus delivery hub 29 to establish a fluid connection between the reservoir 40 and the delivery conduit 18, and such that the outlet port 41 interfaces with the conduit intake 24 by insertion of the conduit intake 24 into the outlet port 41. The bolus delivery hub 29 can include a hub orifice 45 such that the nipple cavity 52 is in fluid communication with the reservoir 40 when the bolus delivery nipple 16 is joined to the feeding bottle 112 and reservoir 40 by the nipple collar 50, and such that fluid 44 can flow from the reservoir 40 into the nipple cavity 52 via the hub orifice 45, thus providing an infant subject 60 with the sensation of a nipple cavity 52 filled with fluid 44 during a feeding transition training session and/or during delivery of a bolus 36 to the infant subject via the delivery conduit 18 of the bolus delivery nipple 16.

Figure 15:
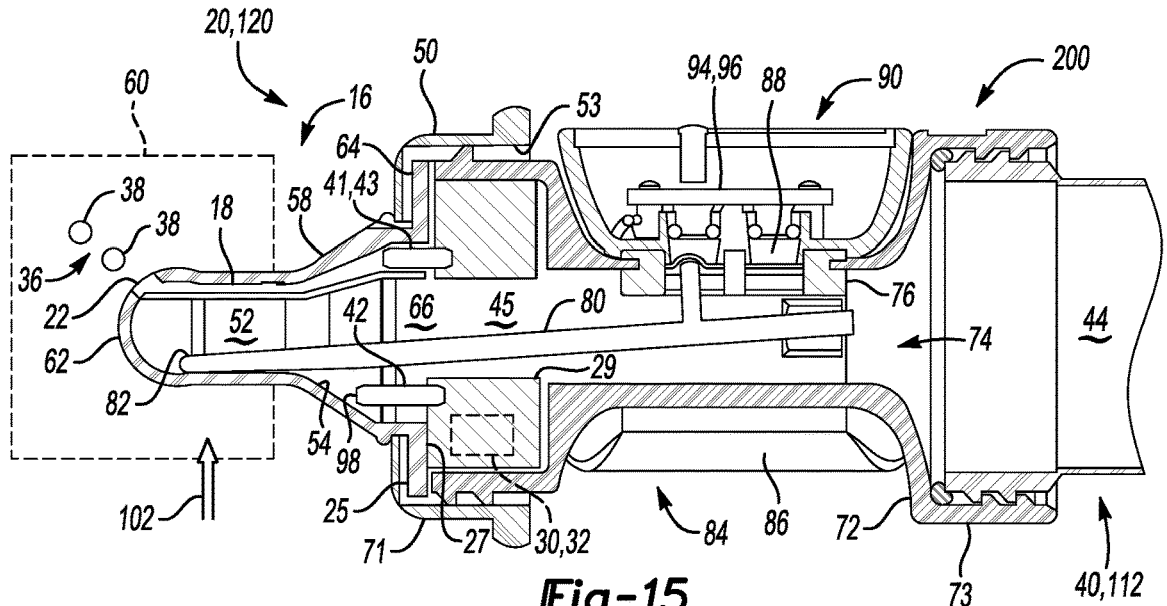
FIG. 15 is a schematic cross-sectional view of an example feeding transition system comprising the example bolus delivery nipple of FIG. 12, an example bolus delivery hub, a feeding performance evaluation coupling device; a fluid reservoir and a nipple collar joining the bolus delivery nipple to the coupling device such that the bolus delivery hub is intermediate a distal end of the coupling device and the flange of the bolus delivery nipple.
Figure 17:
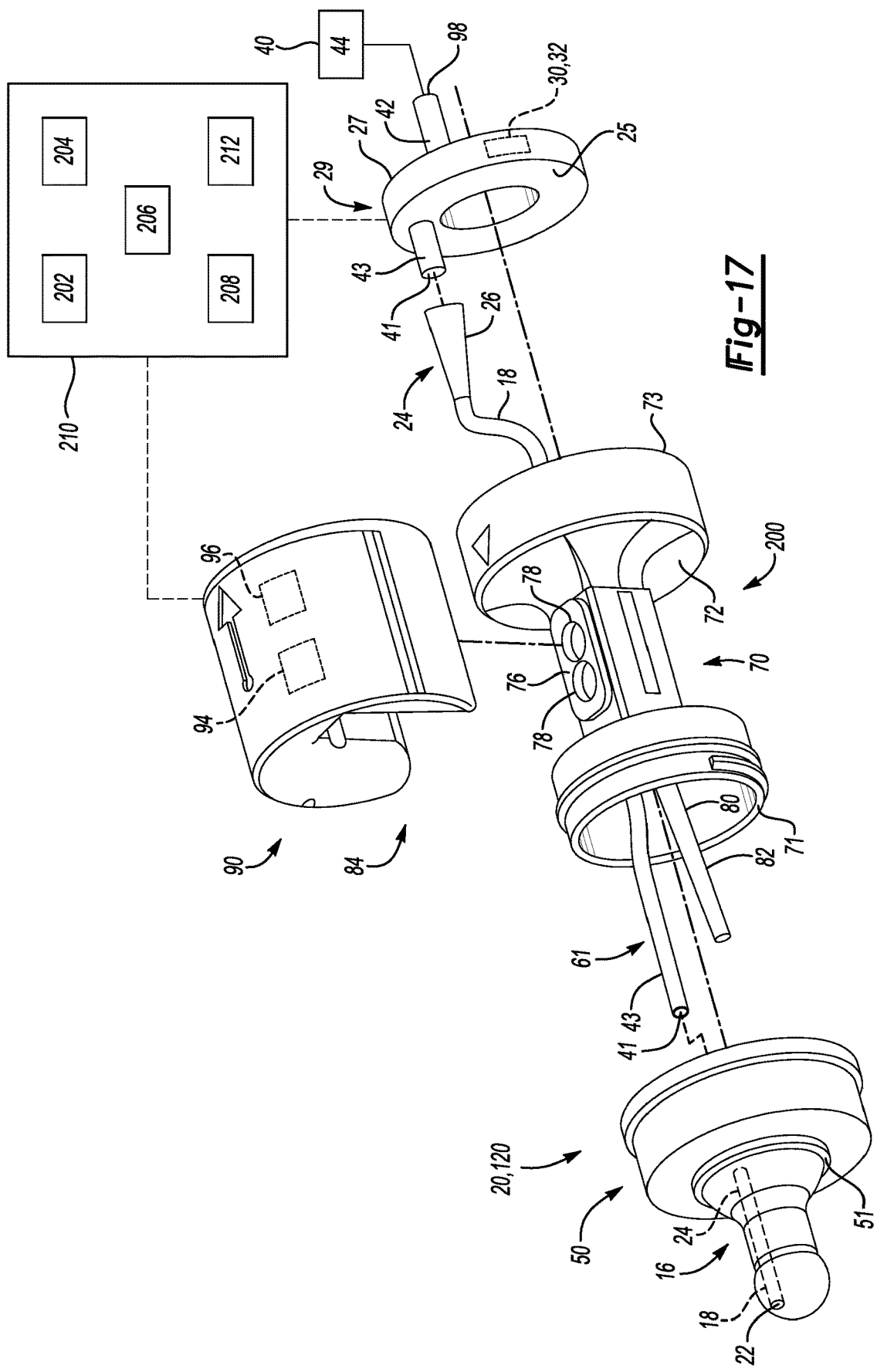
FIG. 17 is a schematic perspective exploded view of an example feeding transition system comprising a feeding performance evaluation system including a coupling device and an evaluation device, further including the example bolus delivery nipple of FIG. 12 joined to a distal end of the coupling device by a nipple collar, an example bolus delivery hub positioned at the proximal end of the coupling device, and a conduit extension interfacing with the bolus delivery nipple and bolus delivery hub and extending through the coupling device such that the bolus delivery hub and the bolus delivery nipple are in fluid communication via the extension conduit.

In the examples shown in FIGS. 7 and 12-17, output of the bolus 36 from the bolus delivery nipple 16 is controlled by the actuator 30 such that, in response to actuation of the bolus delivery apparatus 20 by the actuation, a bolus 36, which can include a plurality of bolus droplets 38, is outputted at a controlled quantity and/or rate from the conduit outlet 22, where the bolus delivery nipple 16, actuator 30 and reservoir 40 comprise a bolus delivery apparatus 20. The actuator 30 can be a manually controlled actuator, such as the syringe plunger as described related to FIG. 7, a hand pump bulb, a squeeze tube, a vial or other manually actuable actuator 30. The actuator 30 can be electronically actuable, as shown in FIGS. 7, 15 and 17, where the actuator 30 can include, for example, a communications interface 32 and a central processing unit (CPU) 34. In one example, the CPU 34 can be configured to actuate the actuator 30 according to instructions received via the communications interface 32 and/or stored in the memory of the CPU 34, which can include instructions as to the amount, frequency, time, etc. of the bolus fluid 44 to be discharged as a bolus 36. In one example, the actuator 30 can be in communication with the evaluation device 210, which may be a mobile device, where the actuator 30 can be, for example, in wireless communication with a communication interface 212 of the evaluation device 210. The evaluation device 210 can include a memory 202, a CPU 204, an evaluation application 206, and a user interface 208, and can be configured for use with a feeding performance evaluation apparatus 200 (see FIGS. 15-17) for evaluating the feeding ability of an infant subject 60. The feeding performance evaluation apparatus 200 can include, as further described herein, a coupling device 70 including a coupling body 72 defining a passage 74 and including a sensor plug 76 attached to a housing 90 including a sensor 94 and communications interface 96 such that the coupling device 70 is configured to measure the tongue strength and tongue movement characteristics of the infant subject 60 during a feeding training session, including the tongue deflection force 102 (see FIGS. 7 and 15) exerted by the tongue of the infant 60 on the nipple wall 54 during a feeding training session. The feeding performance evaluation apparatus 200 including the coupling device 70 and housing 90 are described in additional detail in U.S. non-provisional application Ser. No. 14/665,644 filed Mar. 23, 2015 and published as U.S. application 2015/0208979A1 on Jul. 3, 2015, U.S. non-provisional application Ser. No. 14/166,281 filed Jan. 28, 2014 and issued as U.S. Pat. No. 8,986,226 on Mar. 24, 3015, and U.S. non-provisional application Ser. No. 13/479,640 filed May 24, 2012 and issued as U.S. Pat. No. 8,663,131 on Mar. 4, 2014, all having common inventorship with the subject disclosure and all being incorporated by reference herein in its entirety.

Referring now to FIG. 7 and FIGS. 16-17, in an illustrative example, the evaluation device 210 can have stored in memory 202 an evaluation profile and historical feeding session data for the subject infant 60, which can include instructions for actuating the actuator 30 to deliver a bolus 36 from a bolus delivery apparatus 20 at a predetermined frequency, in a predetermined amount, etc. during a subsequent feeding session. In another example, the bolus delivery apparatus 20 can be operatively connected to the coupling device 90 of the evaluation apparatus 200, as shown in FIGS. 16-17, where the evaluation apparatus 200 can include a communication interface 96 in communication with the communication interface 212 of the evaluation device 210, for example, to send sensor data collected from a sensor 94 of the evaluation apparatus 200 during a feeding session. The sensor data can include, for example, data on a tongue movement of the tongue of an infant 60 (indicated generally by arrow 102 in FIG. 15) exerted by a subject infant 60 on the bolus delivery nipple 16 on a lever end 82 of an intermediate device 80 extending into the nipple cavity 52 of the bolus delivery nipple 16. The tongue movement data can include, for example, tongue force data. The communication of sensor data from the sensor 94 to the evaluation device 210 can occur in real time, such that, in real time, the evaluation device can evaluate the feeding status of the infant subject 60 and output instructions to the actuator 30 based on the sensed feeding status of the infant. For example, in real time, the sensor 94 can detect a decreasing trend in the tongue movement 102 exerted by the infant 60 on the bolus delivery nipple 16 and lever end 82, where a decreasing trend in tongue movement and/or tongue force exerted by the infant 60 can indicate feeding fatigue, and the evaluation application 206 of the evaluation device 210, in response to the sensor data received from the coupling device 70 via communications interfaces 96, 212, can adjust the actuation signal sent to the actuator 30 to decrease the frequency and/or the amount of bolus 36 to be discharged via the delivery conduit 18 to the infant, in response to the sensed fatigue.

FIGS. 15-17 show examples of combinations of the bolus delivery apparatus 20 including a bolus delivery nipple 16, a bolus delivery hub 29, and a conduit extension (see FIG. 17) with the evaluation coupling device 70. In FIGS. 15-17, shown is a coupling body 72 of the coupling device 70 attached at a distal end 71 of the coupling body 72 to a collar 50 such that a lever end 82 of an intermediate device (lever) 80 of the coupling device 70 extends from the coupling body 72 into the nipple cavity 52 of the bolus delivery nipple 16. The coupling body 72 includes a central passage 74 through which fluid 44 can flow, for example, from reservoir 40 configured in the example as a feeding bottle 112 attached to a proximal end 73 of the coupling device 70, as shown in FIGS. 15 and 16, into the nipple cavity 52 of the bolus delivery nipple 16, where the fluid 44 can be received from the nipple cavity 52 into an intake port 42 of a bolus delivery hub 29, via a reservoir interface 98 defined by the intake port 42. The bolus delivery hub 29 is positioned in the passage 42 and interfaces with the proximal face 67 of the flange 64 of the bolus delivery nipple 16 such that the outlet port 41 of the bolus delivery hub 29 is in interfacing contact with the conduit intake 24 of the bolus delivery nipple 16, to deliver fluid 44 to the conduit 18 when actuated by the actuator 30. In the example shown, the actuator 30 includes a communications interface 32 for remote actuation of the actuator 30 by an actuation signal sent to the communications interface 32. The coupling body 72 includes a sensor plug 76 including membranes 78. At least one of the membranes 78 is actuable by the intermediate device 80 in response to a tongue movement 102 (see FIG. 15) exerted on the lever end 82 of the intermediate device 80, for example, during a feeding session by an infant 60 using the device configuration shown in FIGS. 15 and 16. Actuation of the membrane 78 is sensed by a sensor 94 housed in a housing 90 which is fitted to the coupling body 72 as shown in FIG. 15. The sensor 94 outputs a sensor signal to the communication interface 96, which can output the sensor signal to an evaluation device 210 as previously discussed related to FIG. 16. The evaluation device 210 can receive the sensor signal via a communications interface 212 and can output actuation instructions to a communications interface 32 of an electronic actuator 30, as shown in FIGS. 15 and 16, and/or can output actuation instructions to for manual actuation of the actuator 30, for example, via a user interface 208 of the evaluation device 210. The bolus delivery conduit 18, the intake port 42 and the outlet port 41 are positioned in the nipple cavity 52 relative to the lever end 82, where the lever end 82 is in contact with and/or immediately adjacent to the interior surface of the nipple wall 54 to detect deflection of the nipple wall 54 by a tongue movement of the infant 60 during feeding, such that the delivery conduit 18, the intake port 42 and the outlet port 41 do not interfere with movement of the lever end 82. The delivery conduit 18 is positioned such that movement of the lever end 82 does not affect fluid flow through the delivery conduit 18 and/or outputting of a bolus 36 from the conduit outlet 22 to the infant 60.

Referring to FIG. 17, the feeding transition mechanism 120 operates as described for FIGS. 15 and 16, where in the example shown in FIG. 17, the bolus delivery hub 29 is positioned at the proximal end 73 of the device coupling 70, and a extension conduit 61 is used to extend the length of the bolus delivery conduit 18 to provide fluid communication between the delivery conduit 18 of the bolus delivery nipple 16 and the bolus delivery hub 29 and/or a reservoir 40 located remotely from the bolus delivery nipple 16, via the conduit extension 61. In the example shown in FIG. 17, the delivery conduit 18 includes a first end and a second end. The first end of the conduit extension 61 includes a conduit intake 24 which can define an intake coupling 26 configured to interface with the output port 41 of the bolus delivery hub 29 and/or reservoir 40. The second end of the conduit extension 61 includes an output port 41 which can define a conduit interface 43 configured to interface with the conduit intake 24 of the delivery conduit 18 of the bolus delivery nipple 16. In the example shown in FIG. 17, the conduit extension 61 is of sufficient length to extend through the central passage 74 of the coupling device 70 such that the intake coupling 26 defined by the first end of the conduit extension 61 is interfaced with the outlet port 41 of the bolus delivery hub 29 and the conduit interface 43 defined by the second end of the conduit extension 61 is interfaced with the conduit intake 24 of the bolus delivery nipple 16, and such that the outlet port 41 of the bolus delivery hub 29 is in fluid communication with the conduit intake 24 of the bolus delivery nipple 16 via the conduit extension 61.

Figure 18:
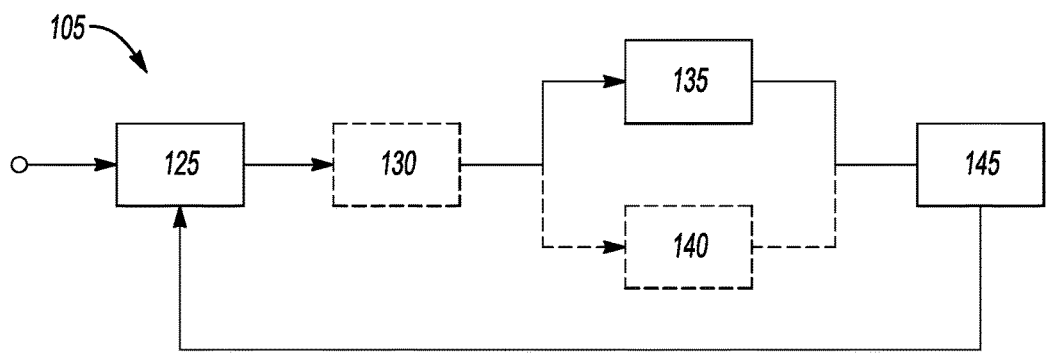
FIG. 18 is a schematic view of an example method for transitioning an infant subject to oral feeding using the feeding transition system of FIG. 1.

Referring now to FIG. 18, an example method for transitioning an infant to oral feeding using the nipple set 10 of FIG. 1 and/or one or more feeding transition mechanisms 120 including at least one nipple 12, 14A, 14B 14C, 16 of the nipple set 10, is provided. The feeding transition method 105 illustrated by FIG. 18 uses one or more of nipples 12, 14, 16 of the nipple set 10 shown in FIG. 1. Optionally, the feeding transition method can use one or more feeding transition mechanisms 120 including a combination of the coupling device 70 and one or more of the nipples 12, 14, 16 of the nipple set 10, and/or the evaluation device 210 described previously herein and further disclosed in additional detail in U.S. non-provisional application Ser. No. 14/665,644 filed Mar. 23, 2015 and published as U.S. application 2015/0208979A1 on Jul. 3, 2015, U.S. non-provisional application Ser. No. 14/166,281 filed Jan. 28, 2014 and issued as U.S. Pat. No. 8,986,226 on Mar. 24, 3015, and U.S. non-provisional application Ser. No. 13/479, 640 filed May 24, 2012 and issued as U.S. Pat. No. 8,663, 131 on Mar. 4, 2014, all having common inventorship with the subject disclosure. The feeding transition method 105 begins at 125 with providing a first feeding transition mechanism 120 including a first nipple selected from the nipple set 10, e.g., where the first nipple is one of a no-flow nipple 12, an ESF nipple 14A, a SLF nipple 14B, a STF nipple 14C, and a bolus delivery nipple 16. The first nipple can be selected based on multiple factors including the feeding development stage of the infant subject 60 being transitioned to oral feeding, the objectives of the first feeding session, which can include an objective of evaluating the feeding ability of the infant subject 60, etc. The first feeding transition mechanism 120 can include a fluid reservoir 40 for providing a fluid 44 to the nipple cavity 52 of the first nipple, and/or, can optionally include the feeding performance evaluation system 200, including the coupling device 70 with the intermediate device 80 inserted into the nipple cavity 52 of the first nipple to sensing tongue movement and feeding behavior of the infant 60, and the evaluation device 210. When the coupling device 70 is included in the first feeding transition mechanism 120, the method proceeds to 130 and the coupling device 70 is paired in communication with the evaluation device 210 via communications interfaces 96, 212, for data transfer from the coupling device 70 to the infant Optionally, at 130, when the first feeding transition mechanism 120 includes a bolus delivery apparatus 20 including an electronic actuator 30, the evaluation device 210 can be paired in communication with the electronic actuator 30 via the communications interfaces 210, 32, for sending actuation signals or instructions from the evaluation device 210 to the electronic actuator 30. At 135, a first feeding session is conducted with the infant subject 60 using the first feeding transition mechanism 120 and observations of the infant subject's feeding performance. The observations can be both quantitative and qualitative, and can include, for example, an assessment of the health of the infant 60, the fatigue rate during the feeding session, the amount of fluid intake by the infant when a fluid is provided either via a flow nipple 14 or bolus delivery nipple 16, the flow rate of the nipple when a flow nipple 14 is used, the bolus size and frequency when a bolus delivery nipple 16 is used, etc. When the coupling device 70 is included in the first feeding transition mechanism 120, the method includes an optional step 140 which is performed concurrently with the feeding session of step 135, and includes collecting and storing to memory 202 sensor data outputted from the coupling device 70, including force deflection data generated by the intermediate device 80 and sensor 94. At step 145, the first feeding session is evaluated, which can include reviewing the quantitative and qualitative observations made at step 135, analyzing the data collected at optional step 140 when the evaluation system 200 including the coupling device 70 is used, assessing the infant's feeding performance quantitatively, qualitatively, and/or in comparison with the goals and objectives established for the first feeding transition session, and/or establishing goals and objectives and/or a plan for the second feeding transition session.

After completing the first feeding transition session, e.g., completing method steps 125, 135, 145 and optionally 130 and 140, the method continues beginning at step 125, with configuring a second feeding transition mechanism 120 including a second nipple selected from the nipple set 10, where the second nipple is one of a no-flow nipple 12, an ESF nipple 14A, a SLF nipple 14B, a STF nipple 14C, and a bolus delivery nipple 16. The second nipple can be selected based on multiple factors including the feeding development stage of the infant subject 60 being transitioned to oral feeding, the objectives of the second feeding session, the evaluation results and/or recommendations from step 145 of the first feeding transition session, etc. The second nipple can be the same type of nipple as was selected and used for the first feeding transition session, for example, where it would be beneficial for consistency and the infant's development to repeat the feeding sequence of the first session, and/or where the evaluation results show minimal developmental progress by the infant during the first session. As described for the first feeding transition session, the feeding transition mechanism 120 can include the coupling device 70 and/or the evaluation device 210 of the evaluation apparatus 200. Once the second feeding transition mechanism 120 including the second nipple is configured, the method proceeds through steps 135 and 140, and optionally, through steps 130 and 140 when the evaluation apparatus 200 is used, concluding in evaluating the quantitative and qualitative observations and results of the second feeding transition session, comparing these with goals and objectives, and/or providing a recommendation for the next transition feeding session.

The method repeats through steps 125-145 until feeding performance goals and objectives are met, which can include development of the feeding capabilities of the infant subject 60 such that the infant subject 60 is transitioned to feeding on their own. Additional sessions may be performed using steps 125-145 after the infant subject 60 has transitioned to feeding on their own, to quantify whether improvements in feeding performance have been sustained, for example.

Various sequences of nipple use can be used in conjunction with the method 105. For example, a no-flow nipple 12 can be used in initial sessions prior to the infant 60 being cleared for oral feeding, then the infant 60 can be transitioned to sessions conducted with a bolus delivery nipple 16. During the initial sessions conducted with the no-flow nipple 12, in one example, the cavity 52 of the no-flow nipple 12 can be filled with sterilized water to provide a resistance, where the nipple cavity 52 can be filled to different heights within the cavity 52 for variable resistances. The infant subject's response to the initial sessions using the no-flow nipple 12 can be gauged and/or quantified using the evaluation system 200 including the coupling device 70, including an analysis of amplitude of the suck and pattern regularity of the suck performed by the infant 60. In one example, the type of liquid used may be varied, to vary resistance of the no-flow nipple 12.

Once cleared for oral feedings, the sessions can be conducted with a bolus delivery nipple 16, using the bolus delivery apparatus 20 including a reservoir 40 and actuator 30 to deliver drops 38 of bolus fluid 44 to the infant 60 via the delivery conduit 18. The size and amount of bolus drops 38, the type of bolus fluid 44, and the flow of the fluid 44 can be controlled for delivery to the infant 60. Fluid delivery control can be based on the clinician, can be controlled via a manual actuator in response visual observation, an instruction or measured feedback, such as data output from the evaluation system 200, etc.

As the infant 60 matures and/or feeding performance improves, the sessions can be conducted with a flow nipple 14, where nipples 14A, 14B, 14C with sequentially increasing flow rates are introduced during the feeding transition sessions. The nipples 14A, 14B, 14C may be introduced sequentially according to increases in flow rate, or may be introduced in a variable order to assess infant response and feeding performance. The use of flow nipples 14A, 14B, 14C can be interspersed with the use of no-flow nipples 12 and bolus delivery nipples 16, such that in some instances, the transition to flow nipples 14 can occur before, after or during the use of no-flow nipples 12 and bolus delivery nipples 16.

The detailed description and the drawings or figures are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims

The invention claimed is:

1. A feeding transition system for transitioning an infant subject to oral feeding, the system comprising:
   a no-flow nipple comprising:
      a nipple wall forming a tip portion and a base portion;
      a nipple cavity defined by the nipple wall;
      a flange including an opening to the nipple cavity;
   wherein the base portion is intermediate the tip portion and the flange;
   wherein the flange is configured for joining the no-flow nipple to a nipple collar; and
   wherein the tip portion is enclosed such that none of a fluid contained in the nipple cavity can flow directly from the nipple cavity through the nipple wall of the tip portion,
   a bolus delivery nipple comprising:
      a second no-flow nipple including:
         a bolus delivery conduit including a conduit intake and a conduit outlet;
      wherein the bolus delivery conduit is disposed in the nipple cavity of the second no-flow nipple;
      wherein the conduit outlet is attached to the nipple wall such that fluid received into the bolus delivery conduit via the conduit intake can flow through the bolus delivery conduit and be outputted from the second no-flow nipple as a bolus;
      wherein the bolus delivery conduit is attached to the nipple wall such that no fluid can flow directly from the nipple cavity through the nipple wall of the tip portion;
   a reservoir in fluid communication with the conduit intake;
   an actuator;
   wherein the actuator is actuable to deliver a predetermined amount of fluid from the reservoir to the bolus delivery conduit such that the predetermined amount of fluid is outputted from the conduit outlet as the bolus;
   a bolus delivery hub including an outlet port;
   wherein the outlet port is configured to interface with the conduit intake such that the conduit intake is in fluid communication with the reservoir via the outlet port;
   a feeding performance evaluation coupling device at least partially disposed within the nipple cavity;
   wherein the feeding performance evaluation coupling device is configured to output a measurement of a tongue movement exerted on the nipple wall;
   the nipple collar;
   wherein the feeding performance evaluation coupling device comprises:
      a coupling body having a proximal end and a distal end;
      wherein the coupling body includes a central passage extending from the proximal end to the distal end;
      a lever including a lever end;
      wherein the lever is positioned in the central passage and pivotably connected to the coupling body;
      wherein the lever end protrudes from the central passage at the distal end of the coupling body; and
      wherein the coupling body is joined to the flange by the nipple collar such that the lever end is disposed within the nipple cavity and such that the lever is pivoted in response to the tongue movement exerted on the nipple wall.

2. The feeding transition system of claim 1, wherein the no-flow nipple is a first no-flow nipple, the system further comprising:
   a flow nipple comprising:
      a third no-flow nipple;
      an aperture formed in the tip portion of the third no-flow nipple such that fluid contained in the nipple cavity can flow directly from the nipple cavity through the nipple wall of the tip portion through the aperture.

3. The feeding transition system of claim 1, wherein the no-flow nipple is a first no-flow nipple, the system further comprising:
   a plurality of flow nipples, each respective flow nipple comprising:
      a respective no-flow nipple further including:
         an aperture formed in the tip portion of the respective no-flow nipple such that fluid contained in the nipple cavity can flow directly from the nipple cavity through the nipple wall of the tip portion through the aperture.

4. The feeding transition system of claim 3, wherein each of the plurality of flow nipples is characterized by a flow rate of fluid through the aperture;
   wherein the plurality of flow nipples further comprises:
      a first flow nipple characterized by a first flow rate of fluid through the aperture of the first flow nipple;
      a second flow nipple characterized by a second flow rate of fluid through the aperture of the second flow nipple; and
   wherein the first flow rate is less than the second flow rate.

5. The feeding transition system of claim 4, wherein the plurality of flow nipples further comprises:
   a third flow nipple characterized by a third flow rate of fluid through the aperture of the third flow nipple; and
   wherein the third flow rate is greater than the second flow rate.

6. The feeding transition system of claim 3, further comprising:
   a cross-sectional area defined by the aperture;
   wherein the plurality of flow nipples comprises:
      a first flow nipple;
      wherein the aperture of the first flow nipple has a first cross-sectional area;
      a second flow nipple;
      wherein the aperture of the second flow nipple has a second cross-section area; and
   wherein the first cross-sectional area is less than the second cross-sectional area.

7. The feeding transition system of claim 6, wherein the plurality of flow nipples further comprises:
   a third flow nipple;
   wherein the aperture of the third flow nipple has a third cross-section area; and
   wherein the third cross-sectional area is greater than the second cross-sectional area.

8. The feeding transition system of claim 1, wherein the conduit outlet is attached to the nipple wall within the tip portion.

9. The feeding transition system of claim 1, further comprising:
   a central axis defined by the bolus delivery nipple;
   a conduit axis defined by the bolus delivery conduit; and
   wherein the conduit axis and the central axis are parallel to each other.

10. The feeding transition system of claim 1, further comprising:
  a central axis defined by the bolus delivery nipple; and
  wherein at least a portion of the bolus delivery conduit is non-parallel to the central axis.

11. The feeding transition system of claim 1, further comprising:
  a central axis defined by the bolus delivery nipple;
  a outlet angle defined by the conduit outlet relative to the central axis; and
  wherein the outlet angle is greater than zero.

12. The feeding transition system of claim 11, wherein the outlet angle is less than ninety degrees.

13. The feeding transition system of claim 11, wherein the outlet angle is greater than 255 degrees and less than 360 degrees.

14. The feeding transition system of claim 1, wherein the conduit outlet is shaped to form the bolus from fluid received into the bolus delivery conduit.

15. The feeding transition system of claim 1, wherein the bolus delivery conduit is integral to the nipple wall.

16. The feeding transition system of claim 1, further comprising:
  a syringe including the reservoir and the actuator;
  the bolus delivery conduit including an intake coupling; and
  wherein the intake coupling is configured to interface with the syringe to receive fluid into the bolus delivery conduit from the syringe.

17. The feeding transition system of claim 1, wherein the bolus delivery hub includes the actuator.

18. The feeding transition system of claim 1, wherein the reservoir is contained in the bolus delivery hub.

19. The feeding transition system of claim 1, wherein the outlet port interfaces with the conduit intake by insertion of the outlet port into the conduit intake.

20. The feeding transition system of claim 1, wherein the outlet port interfaces with the conduit intake by insertion of the conduit intake into the outlet port.

21. The feeding transition system of claim 1, wherein:
  the bolus delivery hub includes a distal hub face;
  the outlet port is in fluid communication with the distal hub face;
  the flange includes a proximal flange face;
  the conduit intake is in fluid communication with the proximal flange face; and
  the outlet port interfaces in fluid communication with the conduit intake by contact of the distal hub face with the proximal flange face.

22. The feeding transition system of claim 1, the bolus delivery hub further comprising:
  an intake port including a reservoir interface to receive fluid into the intake port from the reservoir; and
  wherein the intake port is in fluid communication with the outlet port.

23. A feeding transition system for transitioning an infant subject to oral feeding, the system comprising:
  a no-flow nipple comprising:
    a nipple wall forming a tip portion and a base portion;
    a nipple cavity defined by the nipple wall;
    a flange including an opening to the nipple cavity;
    wherein the base portion is intermediate the tip portion and the flange;
    wherein the flange is configured for joining the no-flow nipple to a nipple collar;
    wherein the tip portion is enclosed such that none of a fluid contained in the nipple cavity can flow directly from the nipple cavity through the nipple wall of the tip portion;
  wherein the no-flow nipple is a first no-flow nipple, the system further comprising:
    a bolus delivery nipple comprising:
      a second no-flow nipple including:
        a bolus delivery conduit including a conduit intake and a conduit outlet;
        wherein the bolus delivery conduit is disposed in the nipple cavity of the second no-flow nipple;
        wherein the conduit outlet is attached to the nipple wall such that fluid received into the bolus delivery conduit via the conduit intake can flow through the bolus delivery conduit and be outputted from the no-flow nipple as a bolus;
        wherein the bolus delivery conduit is attached to the nipple wall such that no fluid can flow directly from the nipple cavity through the nipple wall of the tip portion;
    a reservoir in fluid communication with the conduit intake;
    an actuator;
    wherein the actuator is actuable to deliver a predetermined amount of fluid from the reservoir to the bolus delivery conduit such that the predetermined amount of fluid is outputted from the conduit outlet as the bolus;
    a bolus delivery hub including an outlet port;
    wherein the outlet port is configured to interface with the conduit intake such that the conduit intake is in fluid communication with the reservoir via the outlet port;
    the bolus delivery hub further comprising:
      an intake port including a reservoir interface to receive fluid into the intake port from the reservoir;
      wherein the intake port is in fluid communication with the outlet port;
      the bolus delivery hub including a hub face;
      wherein the hub face is in contact with the flange to enclose the nipple cavity such that the reservoir is defined by the nipple cavity; and
      wherein the reservoir interface is disposed within the nipple cavity.

24. The feeding transition system of claim 1, further comprising:
  wherein the nipple collar comprises a collar aperture and an interior wall;
  the bolus delivery nipple joined to the nipple collar such that the base and tip portions of the bolus delivery nipple protrude through the collar aperture and such that the flange is retained within the collar in contact with the interior wall; and
  wherein the bolus delivery hub is at least partially disposed within the collar such that the flange is intermediate the bolus delivery hub and the interior wall, and such that the outlet port interfaces with the conduit intake.

25. The feeding transition system of claim 1, wherein the bolus delivery hub is disposed between the flange and the distal end of the coupling body such that the outlet port of the bolus delivery hub interfaces with the conduit intake of the bolus delivery conduit.

26. The feeding transition system of claim 1, further comprising:
  a conduit extension comprising:
    a first end and a second end;
    wherein the first end is configured to interface with the outlet port of the bolus delivery hub;
    wherein the second end is configured to interface with the conduit intake of the bolus delivery nipple; and a conduit in fluid communication with the first end and the second end;
wherein the bolus delivery hub is disposed at the proximal end of the coupling body;
wherein the conduit extension extends through the central passage such that first end of the conduit extension is interfaced with the outlet port of the bolus delivery hub and the second end of the conduit extension is interfaced with the conduit intake of the bolus delivery nipple, and such that the outlet port of the bolus delivery hub is in fluid communication with the conduit intake of the bolus delivery conduit via the conduit extension.

27. A method for transitioning an infant subject to oral feeding, the method comprising:
providing a feeding transition system;
wherein the feeding transition system comprises a nipple set;
wherein the nipple set comprises at least one no-flow nipple and at least one flow nipple;
wherein the at least one no-flow nipple comprises:
a nipple wall forming a tip portion and a base portion;
a nipple cavity defined by the nipple wall;
a flange including an opening to the nipple cavity;
wherein the base portion is intermediate the tip portion and the flange;
wherein the flange is configured for joining the no-flow nipple to a nipple collar; and
wherein the tip portion is enclosed such that none of a fluid contained in the nipple cavity can flow directly from the nipple cavity through the nipple wall of the tip portion;
wherein the at least one no-flow nipple includes a first no-flow nipple and a second no-flow nipple;
wherein the at least one flow nipple comprises:
a first flow nipple comprising:
the second no-flow nipple;
an aperture formed in the tip portion of the second no-flow nipple such that fluid contained in the nipple cavity can flow directly from the nipple cavity through the nipple wall of the tip portion through the aperture;
selecting a first nipple from the nipple set;
conducting a first feeding session with the infant subject using the first nipple; and
determining a first feeding response of the infant subject to the first feeding session;
wherein the feeding transition system further comprises:
a feeding performance evaluation system comprising a feeding performance evaluation coupling device;
wherein the feeding performance evaluation coupling device is at least partially disposed within the nipple cavity and configured to output a measurement of a tongue movement exerted on the nipple wall by the infant subject;
the method further comprising:
collecting at least one measurement of the tongue movement exerted on the nipple wall by the infant subject during the first feeding session, using the feeding performance evaluation coupling device; and
determining the first feeding response of the infant subject using the at least one measurement;
wherein the at least one no-flow nipple further comprises a third no-flow nipple;
wherein the first nipple is the third no-flow nipple;
wherein the third no-flow nipple is configured as a bolus delivery nipple comprising:
the third no-flow nipple;
a bolus delivery conduit including a conduit intake and a conduit outlet;
wherein the bolus delivery conduit is disposed in the nipple cavity of the third no-flow nipple;
wherein the conduit outlet is attached to the nipple wall such that fluid received into the bolus delivery conduit via the conduit intake can flow through the bolus delivery conduit and be outputted from the third no-flow nipple as a bolus; and
wherein the bolus delivery conduit is attached to the nipple wall such that no fluid can flow directly from the nipple cavity through the nipple wall of the tip portion;
wherein the feeding transition system further comprises:
a reservoir in fluid communication with the conduit intake;
an actuator;
wherein the actuator is actuable to deliver a predetermined amount of fluid from the reservoir to the bolus delivery conduit such that the predetermined amount of fluid is outputted from the conduit outlet as the bolus;
the method further comprising:
actuating the actuator during the first feeding session to output the bolus to the infant subject;
collecting the at least one measurement of the tongue movement exerted on the nipple wall by the infant subject in response to the bolus, using the feeding performance evaluation coupling device; and
determining the first feeding response of the infant subject to the bolus using the at least one measurement;
wherein the actuator and the feeding performance evaluation system are in communication with each other such that the actuator is actuable by a signal outputted by the feeding performance evaluation system to the actuator;
the method further comprising:
the feeding performance evaluation system outputting the signal to the actuator in response to the at least one measurement of the tongue movement exerted on the nipple wall by the infant subject during the first feeding session.

28. The method of claim 27, further comprising:
selecting, using the first feeding response, a second nipple from the nipple set;
wherein the second nipple is one of the first nipple and another nipple of the nipple set; and
conducting a second feeding session with the infant subject using the second nipple; and
determining a second feeding response of the infant subject to the second feeding session.

29. The method of claim 28, further comprising:
comparing the first and second feeding responses to determine whether a change in oral feeding ability has occurred;
selecting, using the first and second feeding responses, a third nipple from the nipple set;
wherein the third nipple can be one of the first nipple, the second nipple, and another nipple of the nipple set;
conducting a third feeding session with the infant subject using the third nipple; and
determining a third feeding response of the infant subject to the third feeding session.

30. The method of claim 27, wherein the at least one flow nipple comprises:

the first flow nipple and a second flow nipple;

wherein the first flow nipple is characterized by a first flow rate of fluid through the aperture of the first flow nipple;

wherein the second flow nipple is characterized by a second flow rate of fluid through the aperture of the second flow nipple; and wherein the first flow rate is less than the second flow rate.

31. The method of claim 30, wherein the at least one flow nipple further comprises:

a third flow nipple;

wherein the third flow nipple is characterized by a third flow rate of fluid through the aperture of the third flow nipple; and wherein the third flow rate is greater than the second flow rate.

32. The feeding transition system of claim 27, wherein the feeding performance evaluation coupling device comprises:

a lever including a lever end; and wherein the lever end is disposed within the nipple cavity such that the lever is pivoted in response to the tongue movement exerted on the nipple wall;

the method further comprising:

conducting the first feeding session including evaluating the feeding performance of the infant subject using the feeding performance evaluation coupling device.

\* \* \* \* \*